(12) United States Patent
Graham et al.

(10) Patent No.: US 8,512,963 B2
(45) Date of Patent: Aug. 20, 2013

(54) DETECTION AND QUANTITATION OF FULL-LENGTH THIOREDOXIN (TRX) AND TRUNCATED THIOREDOXIN (TRX 80) IN COMPLEX SAMPLES

(75) Inventors: David Raymond Graham, Baltimore, MD (US); Susan Christine Trow, Baltimore, MD (US); Mary Christine Zink, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 120 days.

(21) Appl. No.: 12/953,053

(22) Filed: Nov. 23, 2010

(65) Prior Publication Data
US 2011/0143379 A1 Jun. 16, 2011

Related U.S. Application Data

(60) Provisional application No. 61/264,344, filed on Nov. 25, 2009.

(51) Int. Cl.
*G01N 33/53* (2006.01)

(52) U.S. Cl.
USPC ............................................ 435/7.1; 436/518

(58) Field of Classification Search
None
See application file for complete search history.

(56) References Cited

PUBLICATIONS

Ago et al., (2007) Thioredoxin 1 as a negative regulator of cardiac hypertrophy. Antioxid Redox Signal 9: 679-687.
Altschul et al. (1997) Gapped BLAST and PSI-BLAST: a new generation of protein database search programs, Nucleic Acids Res 25, 3389-3402.
Baker et al. (2006) The antitumor thioredoxin-1 inhibitor PX-12 (1-methylpropyl 2-imidazolyl disulfide) decreases thioredoxin-1 and VEGF levels in cancer patient plasma, J Lab Clin Med 147, 83-90.
Becker et al., (2004). Oxidative stress in malaria parasite-infected erythrocytes: host-parasite interactions. Int J Parasitol 34: 163-89.
Burke-Gaffney et al. (2005) Thioredoxin: friend or foe in human disease?, Trends Pharmacol Sci 26, 398-404.
Clements et al. (2008) The accelerated simian immunodeficiency virus macaque model of human immunodeficiency virus-associated neurological disease: From mechanism to treatment, Journal of Neurovirology 14, 309-317.
Colantonio et al. (2005) Effective removal of albumin from serum, Proteomics 5, 3831-3835.
Coligan et al., (1995) Production of Monoclonal Antibodies, secitons 2.5.1-2.6.7.
Ebrahimian et al., (2008) Thioredoxin in vascular biology: role in hypertension. Antioxid Redox Signal 10: 1127-36.
Follstaedt et al. (2008) Mechanisms of Minocycline-Induced Suppression of Simian Immunodeficiency Virus Encephalitis: Inhibition of Apoptosis Signal-Regulating Kinase 1 Activation, Journal of Neurovirology, 14(5): 376-388.

Fortin et al. (2009) Clinical Quantitation of Prostate-specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests, Mol Cell Proteomics, 8(5): 1006-1015.
Fortin et al. (2009) Multiple reaction monitoring cubed for protein quantification at the low nanogram/milliliter level in nondepleted human serum, Anal Chem 81, 9343-9352.
Fu et al., (2005) A robust, streamlined, and reproducible method for proteomic analysis of seruim by delipidation, albumin and IgG depletion, and two-dimensional gel electrophoresis, Proteomics 5, 2656-2664.
Green et al., (1992) Production of Polyclonal Antisera, Methods in Molecular Bology, 80: 1-4.
Grogan et al., (2000) Thioredoxin, a putative oncogene product, is overexpressed in gastric carcinoma and associated with increased proliferation and increased cell survival. Hum Pathol 31: 475-481.
Harlow et al., (1988) Antibodies: A Laboratory Manual, Cold Spring habor Laboratory Publication, 726.
Holmgren et al. (2010) Thioredoxin and thioredoxin reductase: Curent research with special reference to human diease, Biochem Biophys Res Commun. 396: 120-124.
Ichiki et al., (2005) Thioredoxin suppresses airway hyperresponsiveness and airway inflammation in asthma, Biochem Biophys Res Commun 334: 1141-1148.
Ikegami et al., (2008) Molecular scanning of the gene for thioredoxin, an antioxidative and antiapoptotic protein, and genetic susceptibility to type 1 diabetes, Ann N Y Acad Sci 1150: 103-105.
Jikimoto et al. (2002) Thioredoxin as a biomarker for oxidative strees in patients with rheumatoid arthritis, Mol Immunol 38, 765-772.
Jordan et al., (2005) The thioredoxin-1 inhibitor 1-methylpropyl 2-imidazolyl disulfide (PX-12) decreases vascular permeability in tumor xenografts monitored by dynamic contrast enhanced magnetic resonance imaging. Clin Cancer Res 11: 529-536.
Kalantari et al., (2008) Thioredoxin reductase-1 negatively regulates HIV-1 transactivating protein Tat-dependent transcription in human macrophages. J Biol Chem 283(48): 33183-33190.

(Continued)

*Primary Examiner* — Jacob Cheu
(74) *Attorney, Agent, or Firm* — Stefan J. Kirchanski; Venable LLP

(57) ABSTRACT

The present invention relates, e.g., to a method for detecting a full-length protein and a truncated form (e.g., a naturally occurring cleavage product) thereof, in a sample, comprising optionally denaturing and reducing proteins in the sample, cleaving the proteins into smaller peptides, and detecting a unique peptide identifier for the full-length protein and/or a unique peptide identifier for the truncated protein, in the sample.

In one embodiment of the invention, the full-length protein is thioredoxin (TRX), and the truncated form thereof is its biologically active, C-terminal truncated, 10 kDa cleavage product, TRX 80.

14 Claims, 35 Drawing Sheets

(56) References Cited

PUBLICATIONS

Kinoshita et al. (2007) Thioredoxin prevents the development and progression of elastase-induced emphysema, Biochem and Biophys Res Commun 354: 712-719.

Kishimoto et al. (2001) Serum thioredoxin (TRX) levels in patients with heart failure, Jpn Circ J 65: 491-494.

Kohler et al., (1975) Continuous cultures of fused cells secreting antibody of predefined apecificity, Nature, 256(5517): 495-497.

Lemarechal et al., (2007).Expression and extracellular release of Trx80, the truncated form of thioredoxin, by 10 TNF-alpha- and IL-1beta-stimulated human synoviocytes from patients with rheumatoid arthritis. Clin Sci, 113: 149-155.

Lovell et al., (2000) Decreased thioredoxin and increased thioredoxin reductase levels in Alzheimer's disease brain, Free Radic Biol Med 28(3): 418-427.

Masutani et al., (1992) Dysregulation of adult T-cell leukemia-derived factor (ADF)/thioredoxin in HIV infection: loss of ADF high-producer cells in lymphoid tissues of AIDS patients, AIDS Res Hum Retroviruses 8(9): 1707-1715.

Masutani et al., (2005) The thioredoxin system in retroviral infection and apoptosis, Cell Death Differ 12: 991-998.

Maurice et al. (1999) Expression of the thioredoxin-thioredoxin reductase system in the inflamed joints of patients with rheumatoid arthritis. Arthritis Rheum 42: 2430-2439.

Miwa et al. (2005) Serum thioredoxin and α-Tocopherrol Concentrations in Patients with risk factors, Circ J 69, 291-294.

Miyamoto et al., (2005) Increased plasma levels of thioredoxin in patients with glucose intolerance. Intern Med 44: 1127-1132.

Nakamura et al., (1996) Elevation of plasma thioredoxin levels in HIV-infected individuals. Int Immunol 8: 603-611.

Newman et al., (1994) Opposing regulatory effects of thioredoxin and eosinophil cytotoxicity-enhancing factor on the development of human immunodeficiency virus 1, J Exp Med 180: 359-363.

Okubo et al., (1997) Amelioration of ischemia-reperfusion injury by human thioredoxin in rabbit lung, J Thorac Cardiovasc Surg 113: 1-9.

Pekkari et al. (2000) Truncated thioredoxin is a mitogenic cytokine for resting human peripheral blood mononuclear cells and is present in juman plasma*, J Biol. of Chem., 275(48): 37474-37480.

Pekkari et al. (2001) Truncated thioredoxin (Trx80) induces production of interleukin-12 and enhances CD14 expression in human monocytes, Blood 97, 3184-3190.

Pekkari et al. (2005) Truncated thioredoxin (Trx80) induces differentiation of human CD14+ monocytes into a novel cell type (TAMs) via activation of the MAP kinases p38, ERK, and JNK, Blood 105: 1598-1605.

Sahaf et al. (1997) Thioredoxin expression and localization in human cell lines: Detection of full-length and truncated species, Exp Cell Res 236, 181-192.

Samyn et al., (2005) A new method for C-terminal sequence analysis in the proteomic era, Nature Methods 2(3): 193-200.

Schulze et al., (2004) Hyperglycemia promotes oxidative stress through inhibition of thioredoxin function by thioredoxin-interacting protein, J Biol Chem 279(29): 30369-30374.

Shao et al., (2001) Thioredoxin expression in primary T-cell acute lymphoblastic leukemia and its therapeutic implication, Cancer Res 61: 7333-7338.

Shono et al. (2007) Predominant effect of A-type natriuretic peptide on reduction of oxidative stress during the treatment of patients with heart failure, Circ J 71: 1040-1046.

Silberstein et al. (1989) Purification, physical characteristics, and partial amino acid sequence of an active polypeptide1, The Journal of Immunology, 143(3): 979-983.

Silberstein et al., (1987) Characterization of a factor from the U937 cell line that enhances the toxicity of human eosiniphils to schistosoma mansoni larvae1, The Journal of Immunology, 138(9): 3042-3050.

Sumida et al., (2000) Serum thioredoxin levels as an indicator of oxidative stress in patients with hepatitis C virus infection, J Hepatol 33: 616-622.

Takagi et al., (1998) Expression of thioredoxin is enhanced in atherosclerotic plaques and during neointima formation in rat arteries, Lab Invest 78: 957-966.

Tanito et al., (2004) Enhanced oxidative stress and impaired thioredoxin expression in pontaneously hypertensive rats, Antioxid Redox Signal 6: 89-97.

Tao et al., (2006) Thioredoxin reduces post-ischemic myocardial apoptosis by reducing oxidative/nitrative stress, Br J Pharmacol 149: 311-318.

Van Laer et al., (2002) Thioredoxin and protein nitrotyrosine in bone marrow supernatant from patients with human immunodeficiency virus infection, J Investig Med 50: 10-18.

Witwer et al. (2009) Coordinated regulation of SIV replication and immune responses in the CNS, PLoS ONE 4(12), e8129.

Yamada et al., (1996) Increased expression of thioredoxin/adult T-cell leukemia-derived factor in cisplatin-resistant human cancer cell lines, Clin Cancer Res 2: 427-432.

Yamada et al., (2003) Elevated serum levels of thioredoxin in patients with acute exacerbation of asthma, Immunol Letter, 86: 199-205.

Yamamoto et al., (2003) Inhibition of endogenous thioredoxin in the heart increases oxidative stress and cardiac hypertrophy. J Clin Invest 112: 1395-1406.

Yoshida et al. (1999) Involvement of thioredoxin in reheumatoid arthritis: Its costimulatory roles in the TNF-α-induced production of IL-6 and IL-8 from cultured synovial fibroblasts J 30 Immunol1 163: 351-358.

Zink et al., (2005) Neuroprotective and anti-human immunodeficiency virus activity of minocycline, JAMA 293(16): 2003-2011.

| Full Length Thioredoxin | |
|---|---|
| Sequence: | MVKQIESKTAFQEALDAAGDKLVVVDFSATWCGPCKM<br>IKPFFHSLSEKYSNVIFLEVDVDDCQDVASECEVKCM<br>PTFQFFKKGQKVGEFSGANKEKLEATINELV (SEQ ID NO:3) |
| Shared<br>CNBr<br>peptides: | VKQIESKTAFQEALDAAGDKLVVVDFSATWCGPCK[M] (SEQ ID NO:5)<br>IKPFFHSLSEKYSNVIFLEVDVDDCQDVASECEVKC[M] (SEQ ID NO:6) |

[C-terminal M can be modified to a homoserine lactone (HSL) residue by CNBr cleavage]

FIG. 1A

TRX80

MVKQIESKTAFQEALDAAGDKLVVVDFSATWCGPCKM
IKPFFHSLSEKYSNVIFLEVDVDDCQDVASECEVKCM
PTFQFFK (SEQ ID NO:4)

FIG. 1B 1 ng TRX or
10 ng TRX80
in 100 ug plasma

| Peptide | Q1 | Q3 | fmole peptide | CV (%) | Accuracy (%) |
|---|---|---|---|---|---|
| TRX80 (2+) | 461.75 | 724.39, 825.44 (sum) | 2 (LOQ) | 8.96 | 107.06 |
| | | | 10 | 5.20 | 94.48 |
| TRX (6+) | 588.33 | 659.76 | 10 (LOQ) | 19.11 | 97.10 |
| | | | 20 | 11.12 | 83.48 |
| TRX (6+) | 588.33 | 824.44 | 10 (LOQ) | 12.89 | 97.11 |
| | | | 20 | 11.60 | 82.43 |
| TRX (5+) | 705.79 | 824.44 | 10 | 14.13 | 101.67 |
| | | | 20 | 16.69 | 107.91 |

FIG. 3E

| Peptide | Sum of MRM | fmole peptide | CV(%) | Accuracy(%) |
|---|---|---|---|---|
| TRX80 (2+) | 461.75/724.39 | 0.5 (LLOQ) | 8 | 92 |
|  | 461.75/825.44 |  |  |  |
| TRX (6+) | 588.33/659.76 | 1 (LLOQ) | 16 | 115 |
| TRX (5+) | 705.79/824.44 |  |  |  |

FIG. 4C

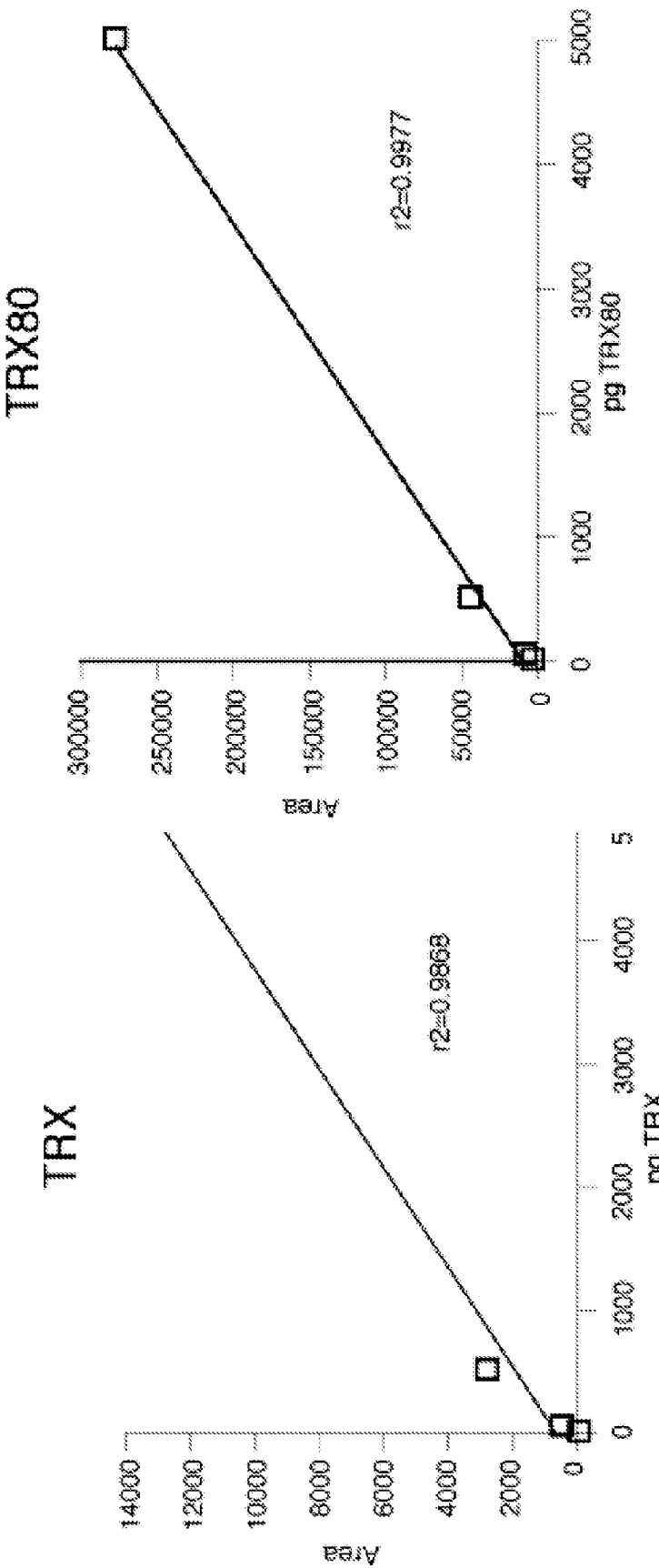

DETECTION AND QUANTITATION OF FULL-LENGTH THIOREDOXIN (TRX) AND TRUNCATED THIOREDOXIN (TRX 80) IN COMPLEX SAMPLES This application claims the benefit of the filing date of U.S. provisional application 61/264,344, filed Nov. 25, 2009, which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Jan. 17, 2011, is named 22429323.txt and is 9,987 bytes in size.

FIELD OF THE INVENTION

The present invention relates, e.g., to a method for detecting two forms of a protein in a sample, using unique peptide identifiers for the two forms of the protein.

BACKGROUND INFORMATION

Thioredoxin (TRX) is a 12 kDa redox cycling enzyme that is ubiquitously expressed in all cell types and is part of a key system for maintaining a reducing intracellular environment, working in a coordinate manner with thioredoxin reductase and NADPH (collectively referred to as the TRX system). TRX plays a role in regulating many different signaling processes, including cell cycle signaling, apoptosis, and glucose metabolism (Holmgren et al. (2010) *Biochem Biophys Res Commun.* 396, 120-124). Oxidative stress leads to TRX upregulation, which then can be secreted by a yet-undefined leaderless pathway. TRX 80, a 10 KDa cleavage product of secreted TRX thought to be composed of the 80 N-terminal amino acids, is produced mainly from cleavage of secreted TRX by activated monocytes/macrophages (Silberstein et al. (1987) *J Immunol* 138, 3042-3050; Silberstein et al. (1989) *J Immunol* 143, 979-983). TRX 80 has monocyte chemoattractant activity and induces differentiation and activation of monocytes to a highly inflammatory phenotype that produces TNFα, IL-1β, IL-6 and IL-8, termed the TRX 80 activated monocyte (TAM) (Pekkari et al. (2005) *Blood* 105, 1598-1605). These cells also upregulate the costimulatory molecule CD86, and when cocultured with T cells produce IL-12 and aid in stimulating interferon-γ production (Pekkari et al. (2005) (supra); Pekkari et al. (2001) *Blood* 97, 3184-3190), suggesting that TAMs facilitate the generation of TH1 (proinflammatory) lymphocytes.

Increased plasma TRX levels have been demonstrated in many disease conditions, including heart failure, cardiomyopathy, cancer, asthma, and rheumatoid arthritis, among others, and are thought to be highly indicative of oxidative stress (Yoshida et al. (1999) *J Immunol* 163, 351-358; Kishimoto et al. (2001) *Jpn Circ J* 65, 491-494; Jikimoto et al. (2002) *Mol Immunol* 38, 765-772; Yamada et al. (2003) *Immunol Lett* 86, 199-205; Miwa et al. (2005) *Circ J* 69, 291-294; Grogan et al. (2003) *Hum Pathol* 31, 475-481). TRX has been tested as an oxidative stress marker in a study examining of the administration of A-type natriuretic peptide to reduce oxidative stress in heart failure patients (Shono et al. (2007) *Circ J* 71, 1040-1046).

Examination of TRX 80 levels in human disease or in model systems has been somewhat limited to date. The cleavage of TRX to TRX 80 may have profound influence on local sites of oxidative stress. TRX 80 levels were shown to be highly variable in plasma of a small number of presumed-healthy donors (Pekkari et al. (2000) *J Biol Chem* 275, 37474-37480). Additionally, production of TRX 80 by synoviocytes cultures from patients with rheumatoid arthritis (RA) has been demonstrated (Lemarechal et al. (2007) *Clin Sci (Lond)* 113, 149-155). Elevated levels of secreted TRX previously have been associated with RA (Jikimoto et al. (2002) (supra)), and in the aforementioned study by Lemarechal and colleagues, TRX 80 was produced at basal levels by cultured synovial cells obtained from RA patients, but not from osteoarthritis patients, with production increased by IL-1β and/or TNF-α stimulation. This suggests a role for TRX 80 production in the infiltration and proliferation of immune cells that are hallmarks of RA.

Several experimental approaches have been used to identify TRX and/or TRX 80 in biological samples, each with its own strengths and limitations. Due to their different functions, it is important to distinguish TRX from TRX 80. However, as TRX 80 is derived from the same amino acid sequence as TRX and they are relatively close in size (12 vs. 10 kDa), it can be difficult to clearly resolve them in a standard immunoblotting assay. Even antibodies developed to specifically recognize TRX 80 in its native nondenatured form may recognize both TRX 80 and TRX in western blot (Sahaf et al. (1997) *Exp Cell Res* 236, 181-192).

ELISA is frequently used to detect TRX. While potentially informative, most ELISAs may crossreact to TRX 80. One group has designed an ELISA that specifically detects the truncated form TRX 80. However, this assay still shows a very small level of cross reactivity for the full length protein (Pekkari et al. (2000) (supra)), which can be problematic if TRX 80 needs to be accurately monitored and is present at much lower levels than TRX.

Other TRX properties may contribute to inaccurate quantitation by immunologic detection. In plasma, TRX 80 may be present in protein dimers (Pekkari et al. (2000) (supra)). TRX also can be bound to other proteins such as albumin, hindering its detection in nondenaturing sample processing methods.

To clearly define a role for TRX in disease, and to use the detection of TRX and/or TRX 80 to diagnose a disease, monitor its progress, or the like, it is important to be able to simultaneously monitor the presence of both TRX forms in a quantitative capacity in complex samples, including plasma and tissue homogenates. There is a need for an assay that can detect the two forms of TRX, unambiguously and quantitatively, e.g. within the same sample.

DESCRIPTION OF THE DRAWINGS

FIGS. 1A-1F shows a reference chart for TRX and TRX 80. The sequences of the unique peptides produced by CNBr digestion are provided for both TRX and TRX 80, as well as the resulting MS peaks obtained by MALDI and their MS/MS spectra with labeled b and y ions (representative spectra shown). The sequence of full length thioredoxin is SEQ ID NO:3. The sequence of TRX 80 is SEQ ID NO:4. The sequences of the shared CNBr peptides are SEQ ID NO:5 (upper) and SEQ ID NO:6 (lower). The sequence of the unique peptide for full length TRX is SEQ ID NO:1. The sequence of the unique peptide for TRX 80 is SEQ ID NO:2. Synthetic peptide standards containing heavy labeled lysine (SEQ ID NOS:34-35, respectively, in order of appearance) (*K, $^{13}C_6$ $^{15}N_2$) were later produced for these same sequences to be used for quantitation in an MRM assay, as is discussed elsewhere herein.

FIGS. 3A-3E shows LC-MRM quantitation curves in plasma. MRM transitions were monitored for dilutions of heavy standard peptides in CNBR-digested plasma (1-10,000 fmole peptide in 2 µL of plasma protein). XICs are shown at the lower limit of quantitation, defined by CV<20% and accuracy between 80-120%). Curves were produced in triplicate using high-flow LC followed by MRM on the QTRAP 5500 system.

FIGS. 4A-4C shows LC-MRM quantitation curves in CSF. MRM transitions were monitored for dilutions of heavy standard peptides in CNBR-digested CSF. XICs are shown at the lower limit of quantitation (LLOQ, defined by CV<20% and accuracy between 80-120%). Curves were produced in triplicate using high-flow LC followed by MRM on the QTRAP 5500 system.

FIGS. 7A-7F shows the limits of detection of unique peptides from CNBr-digested TRX and TRX 80 by MALDI-TOF. Both peptides were clearly detected from digests of 50 ng of recombinant protein down to 5 pg, with peaks of changing intensity (spectra labeled with area under the curve and signal to noise). The identities of these peaks were then confirmed by MS/MS. The areas under the curve for the peaks are plotted, showing detection in a linear range from 5 pg to 5 ng of protein.

DESCRIPTION

Figure 1C:
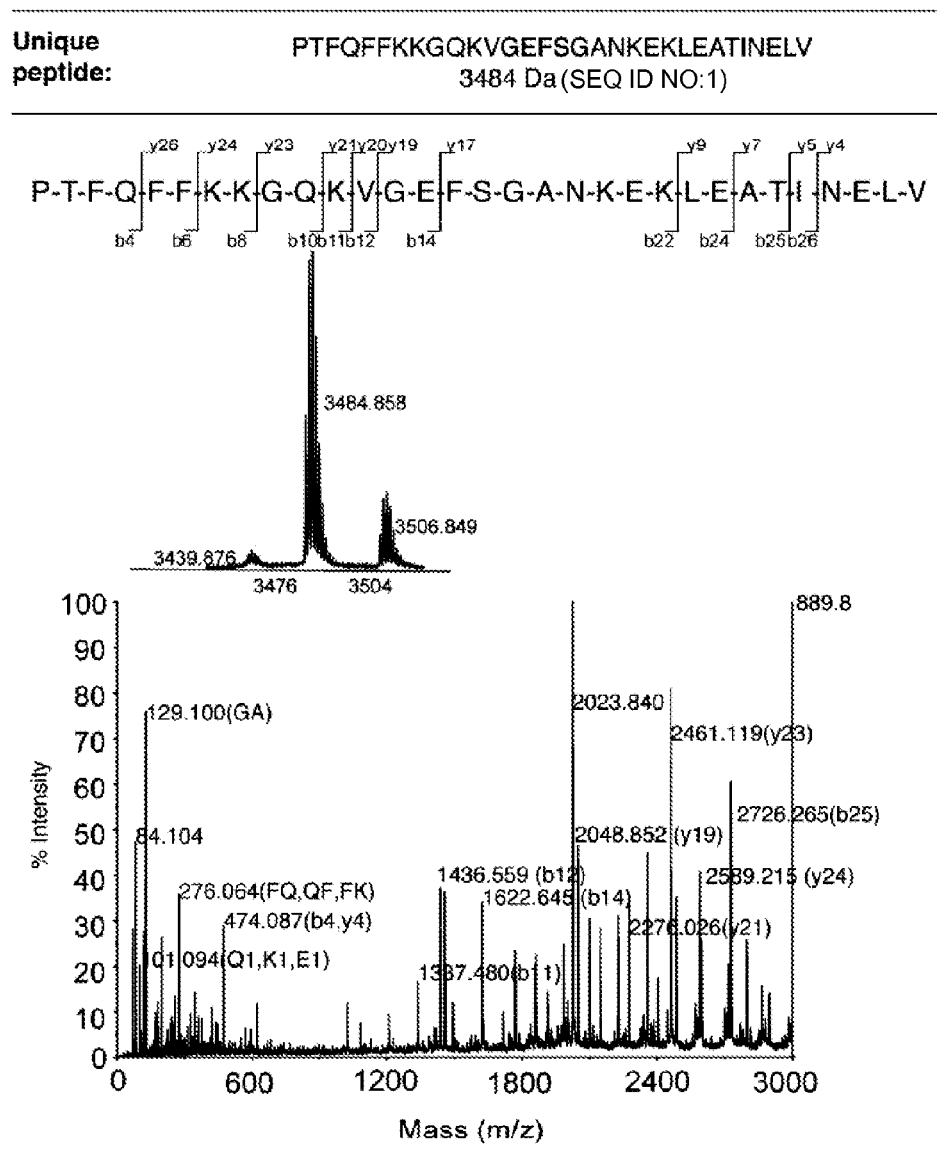
Figure 1D:
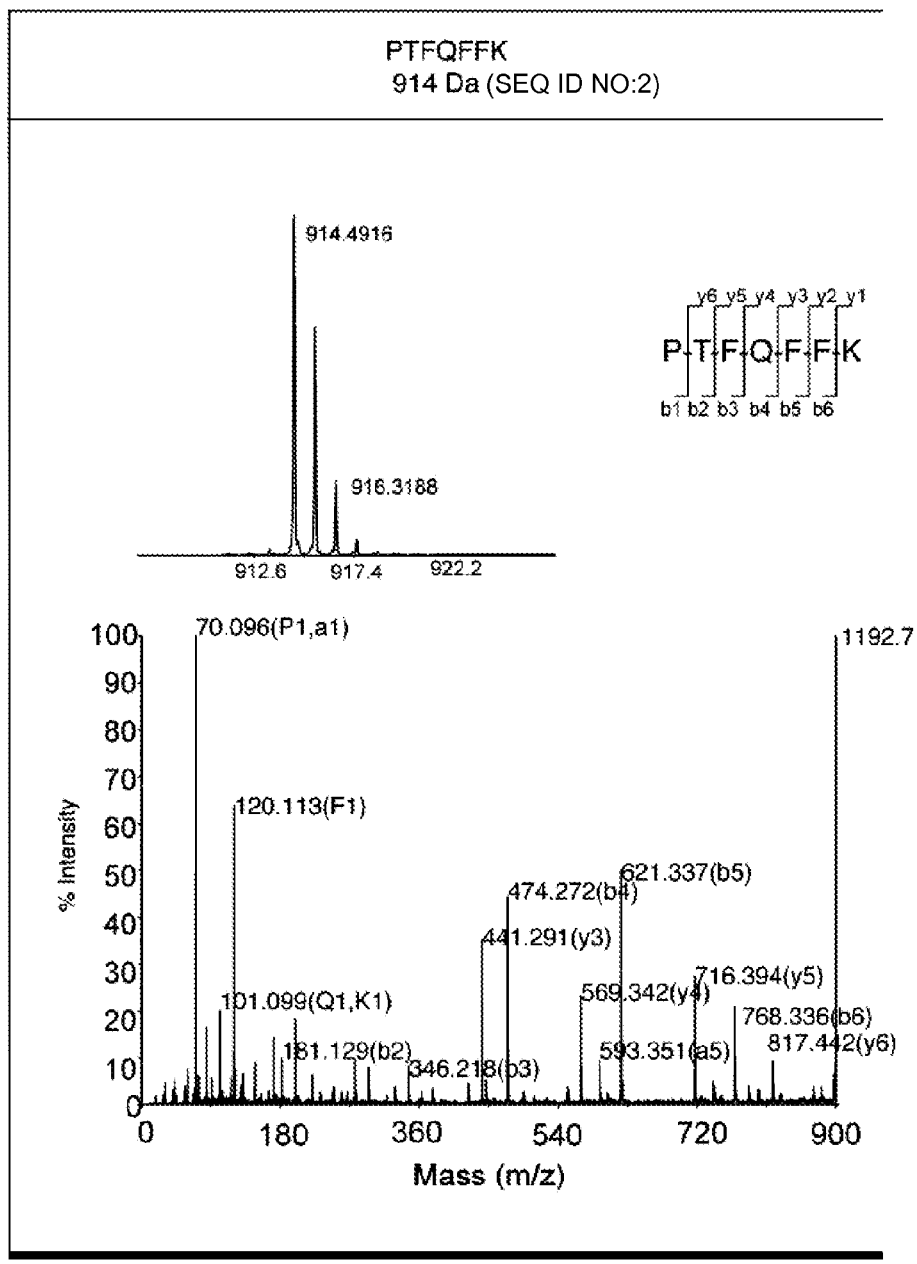
Figure 1E:
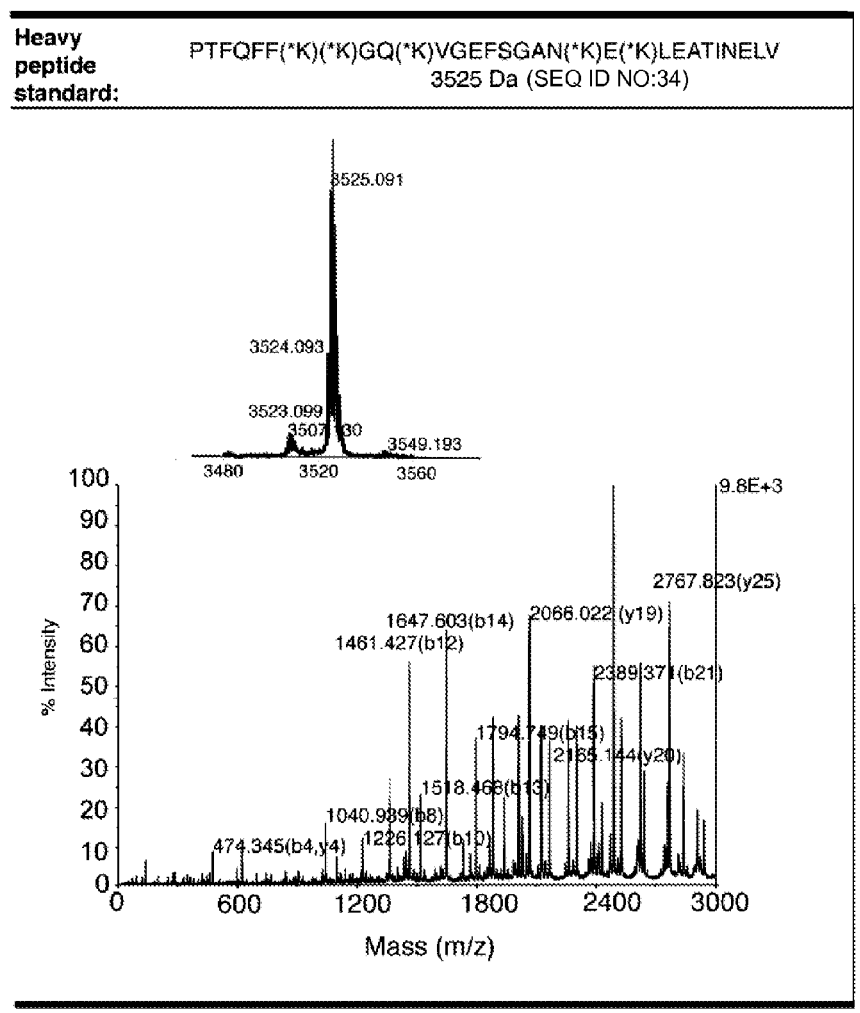
Figure 1F:
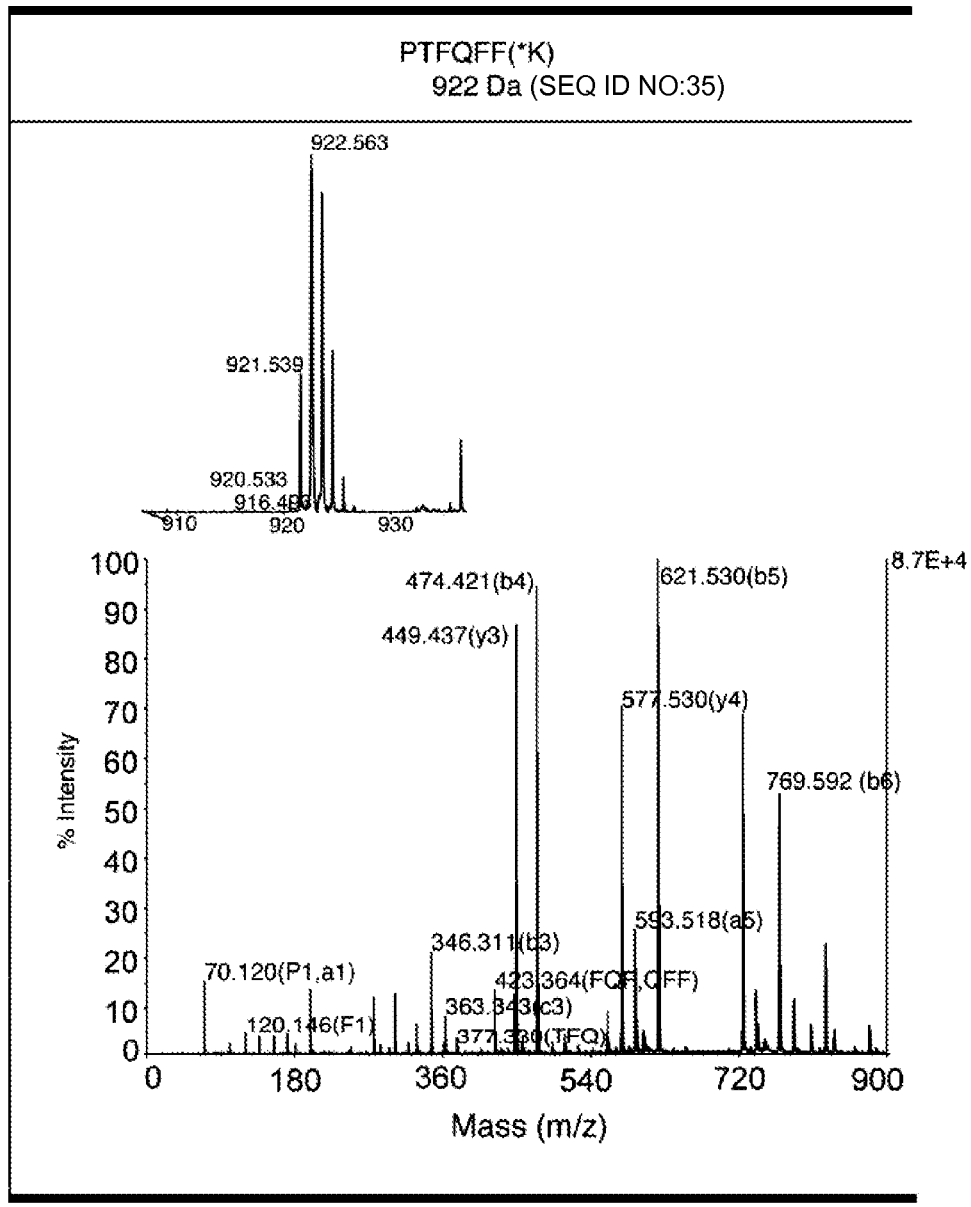
Figure 2A:
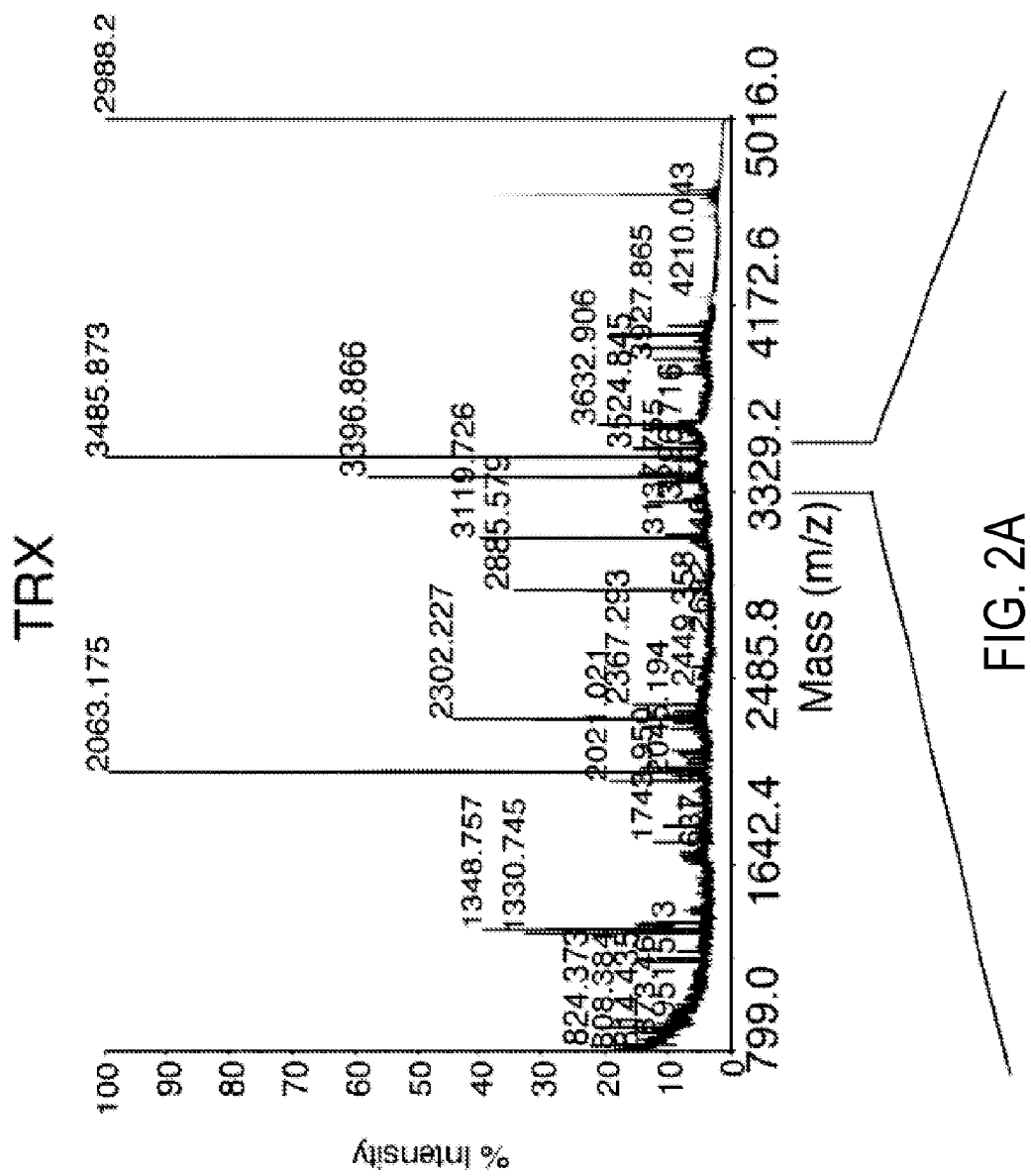
FIGS. 2A-2F shows an experiment in which CNBr digests of recombinant TRX and TRX 80 spiked into 100 µg of CNBr-digested whole human plasma, in consecutive 10 fold dilutions, were fractionated by HPLC-SCX. The identifying peptide for TRX 80 (914 kDa) consistently eluted at 9 minutes on a 35 minute linear gradient (0-350 mM KCl) and was detected at levels down to 10 ng from the complex plasma mixture, while that for TRX (3484 kDa) eluted at 34 minutes and was detected down to 1 ng (representative spectra shown, experiment performed in duplicate).
Figure 2B:
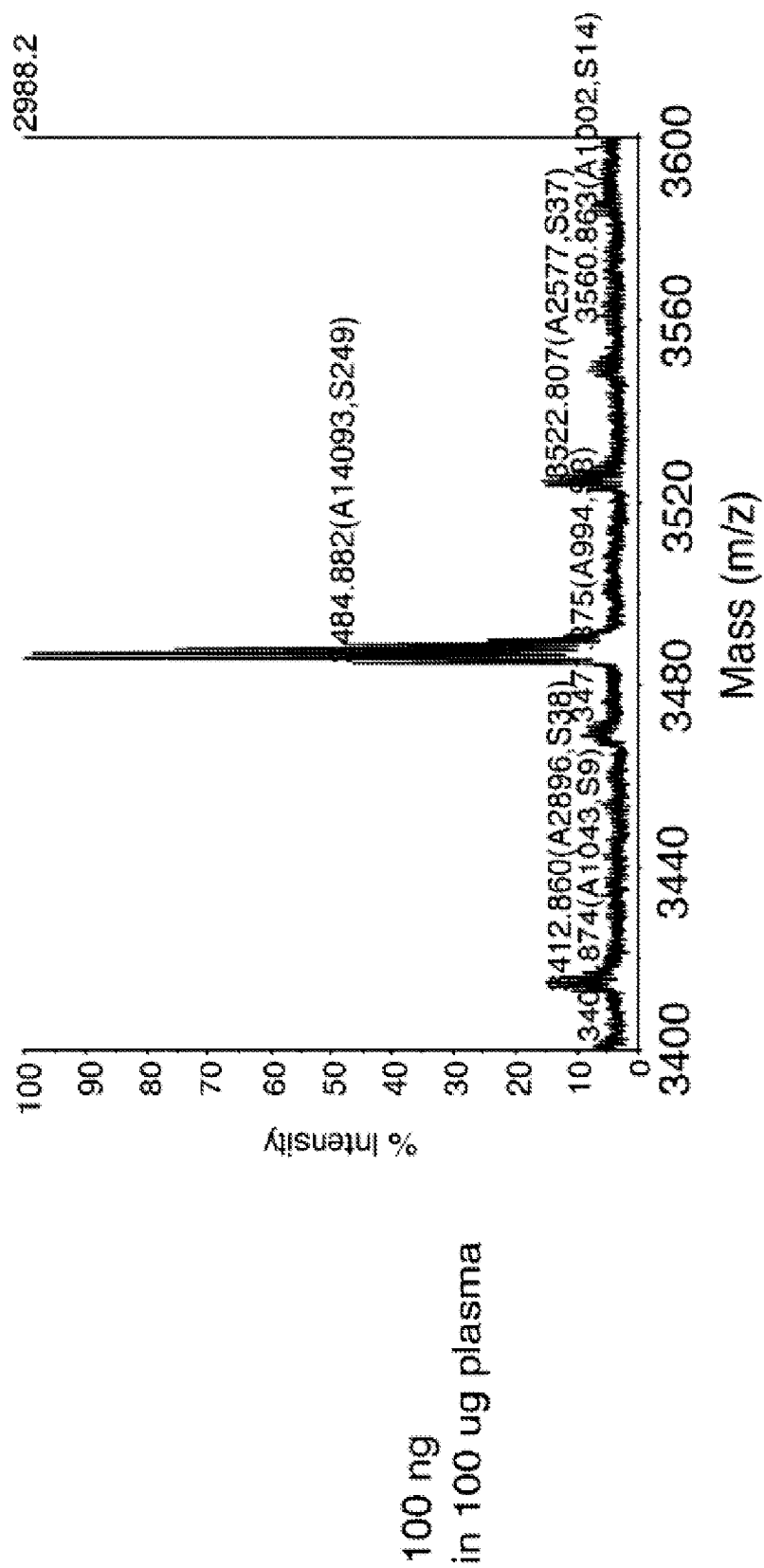
Figure 2C:
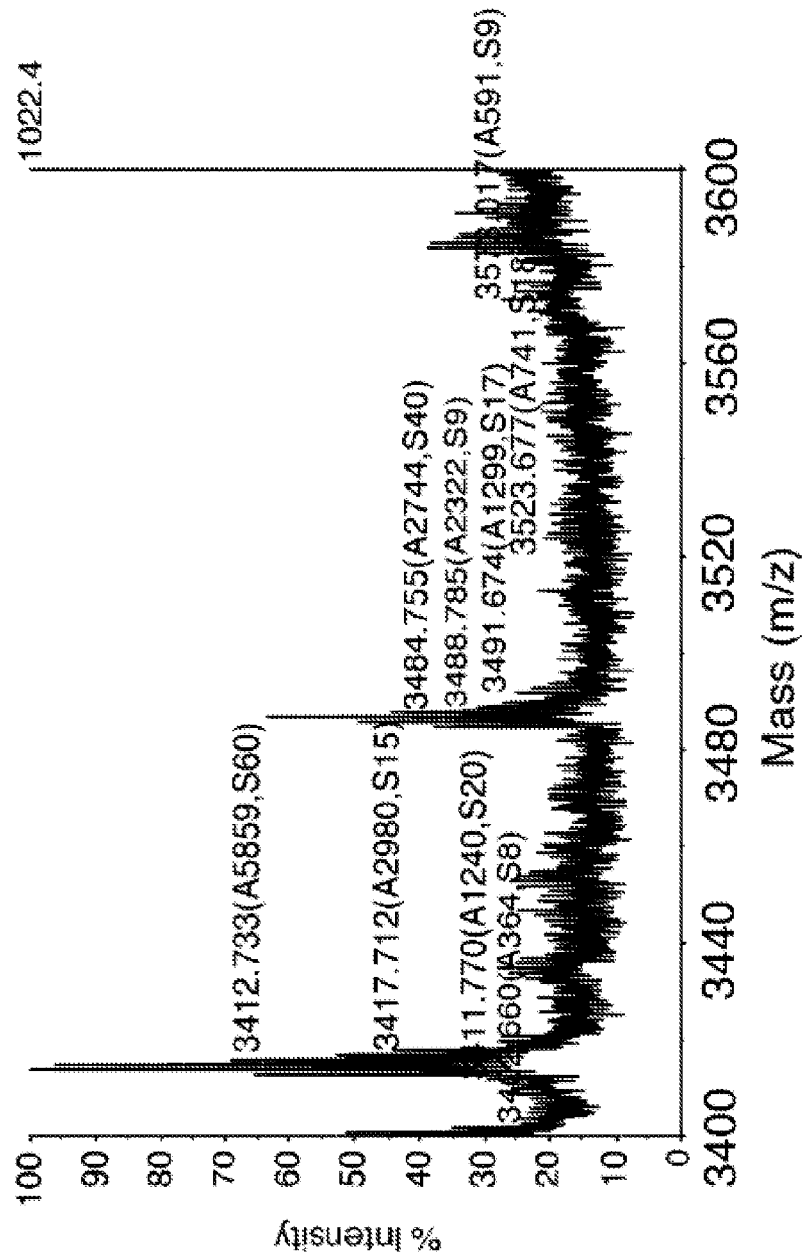
Figure 2D:
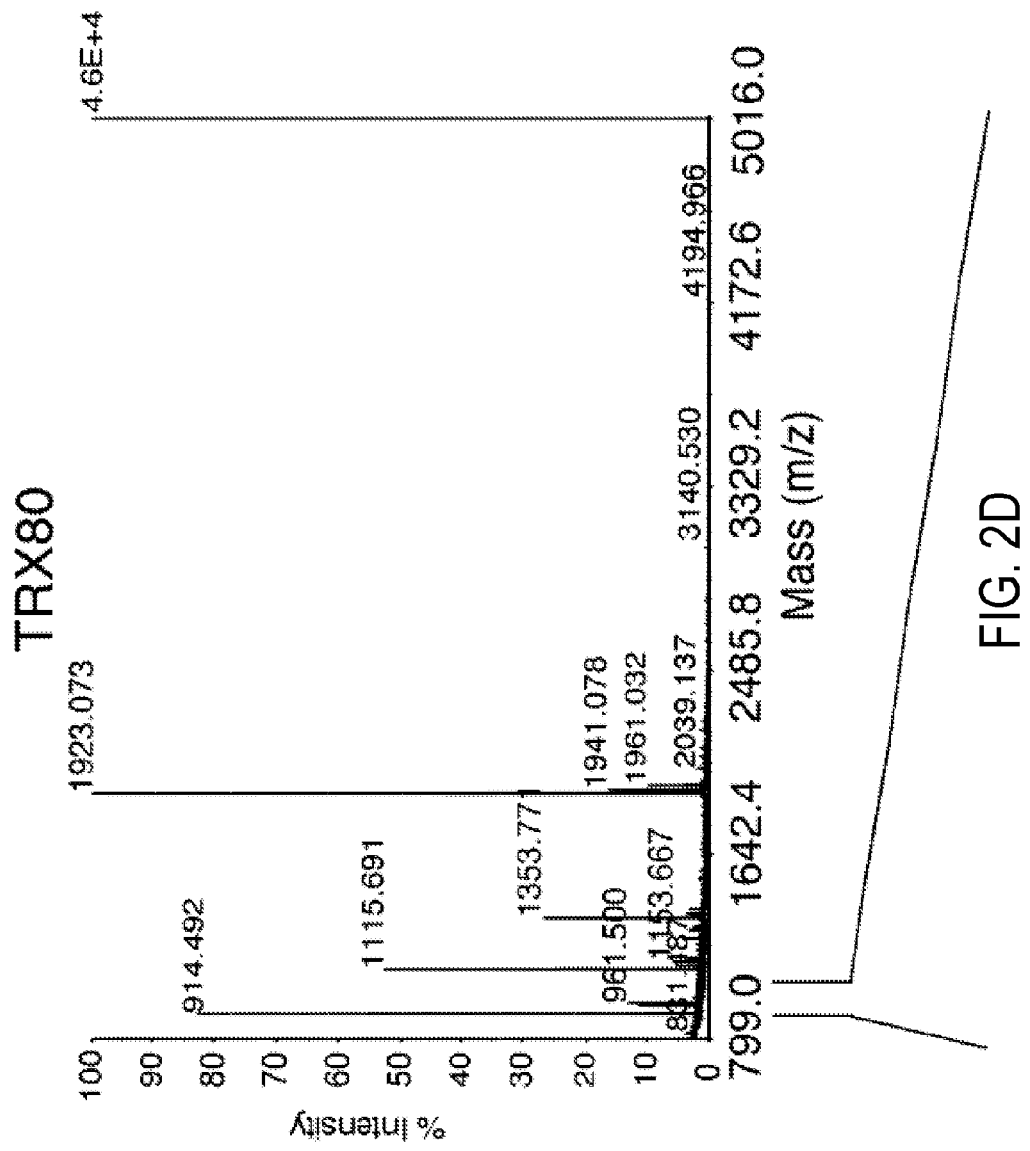
Figure 2E:
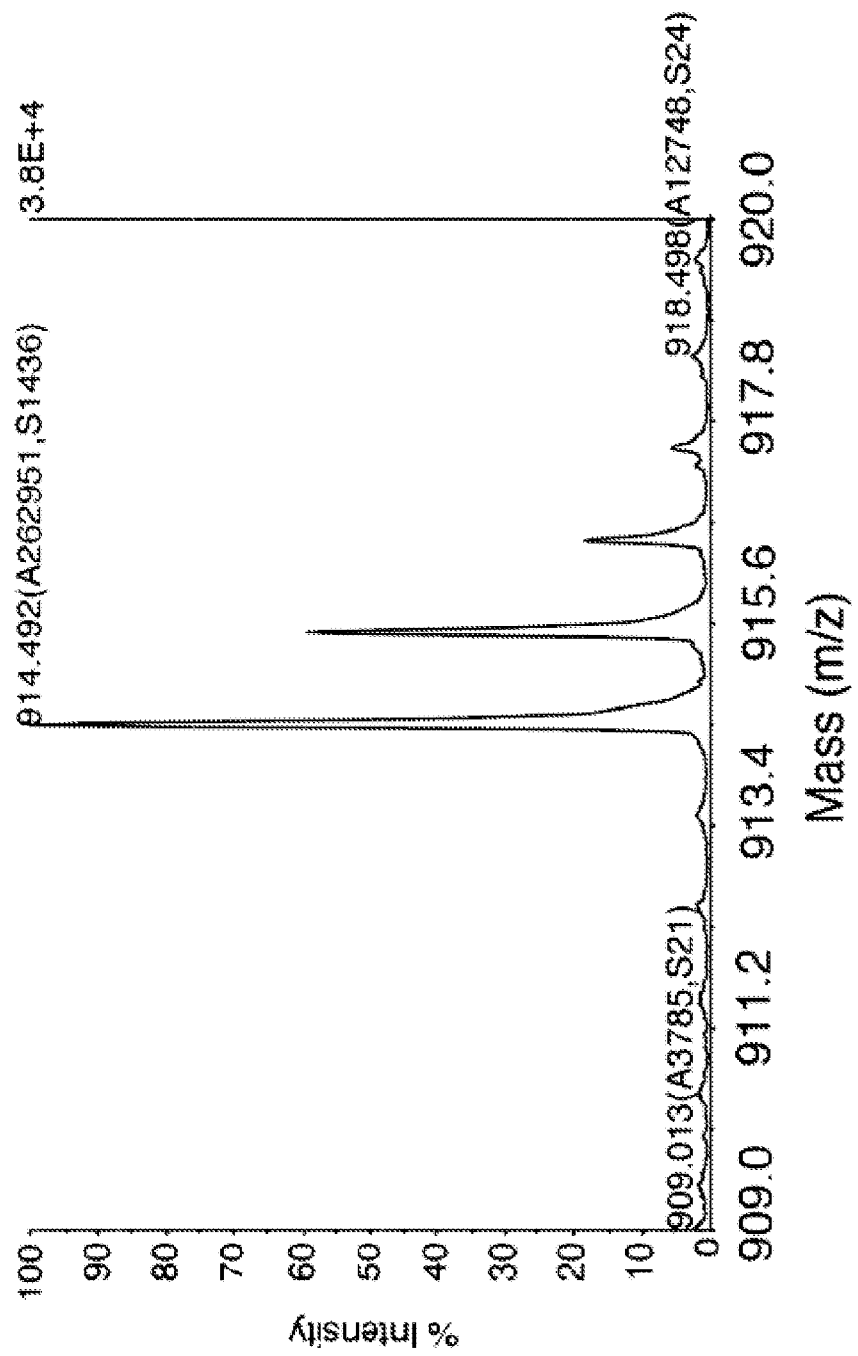
Figure 2F:
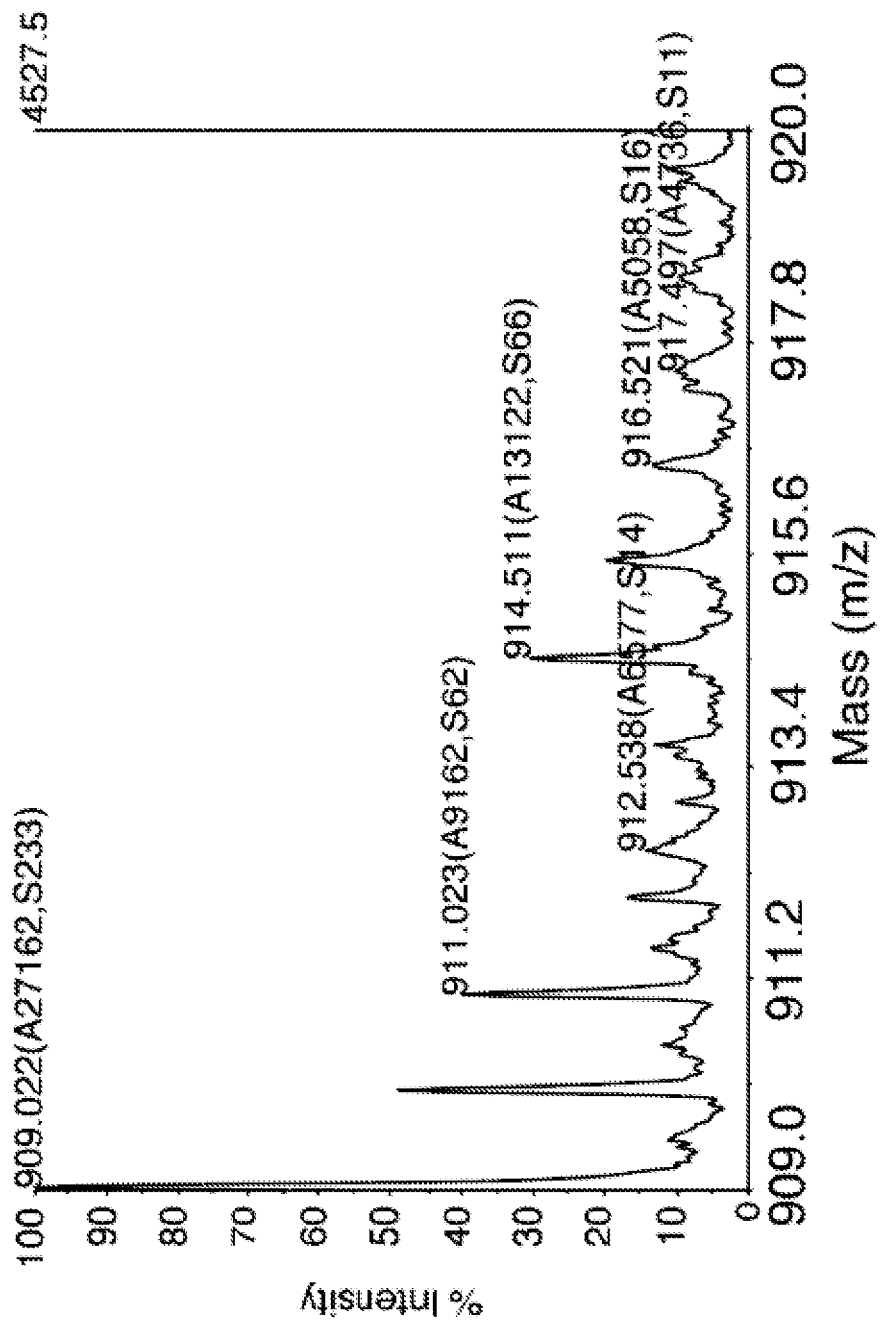
Figure 3A:
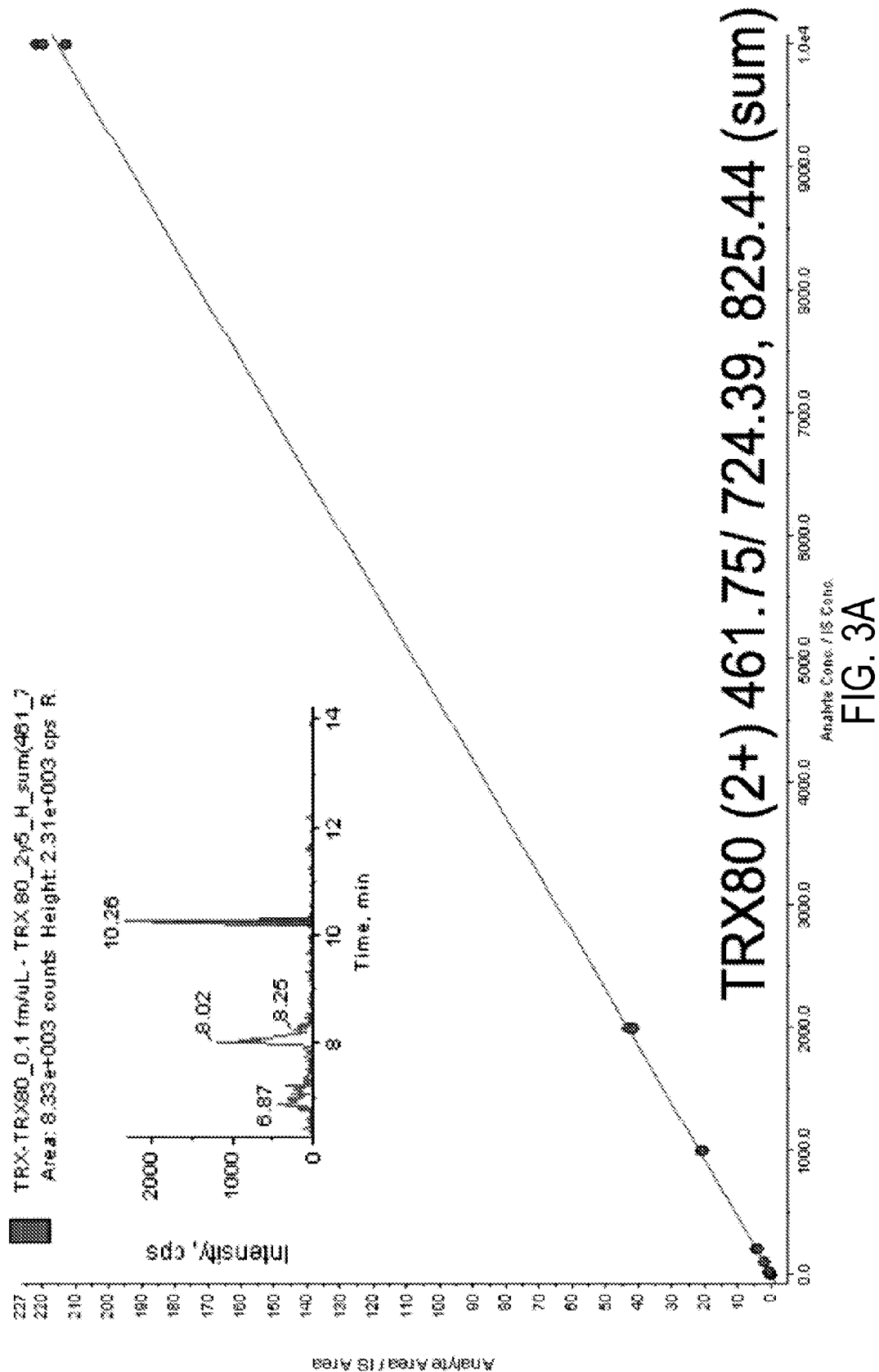
Figure 3B:
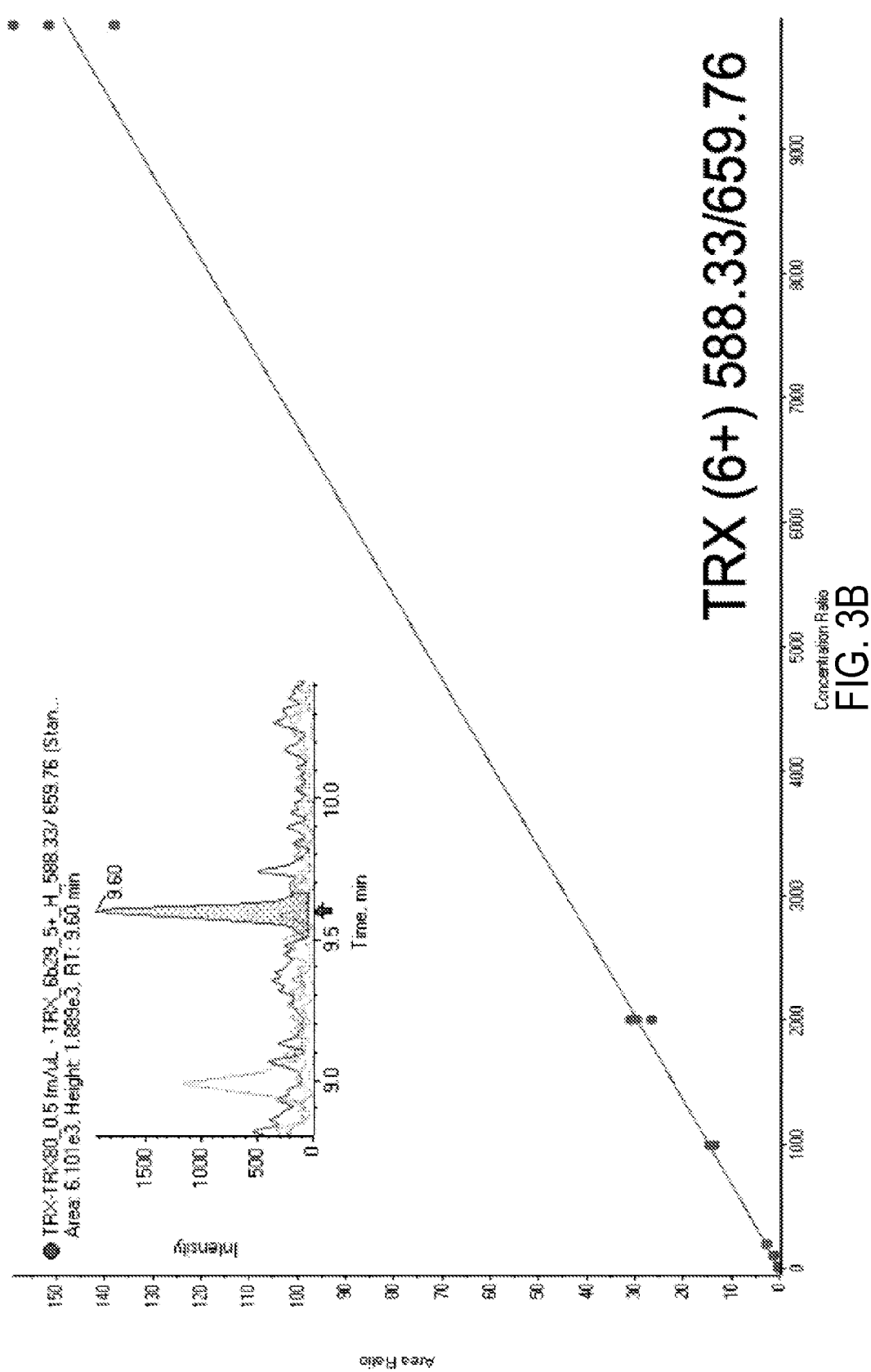
Figure 3C:
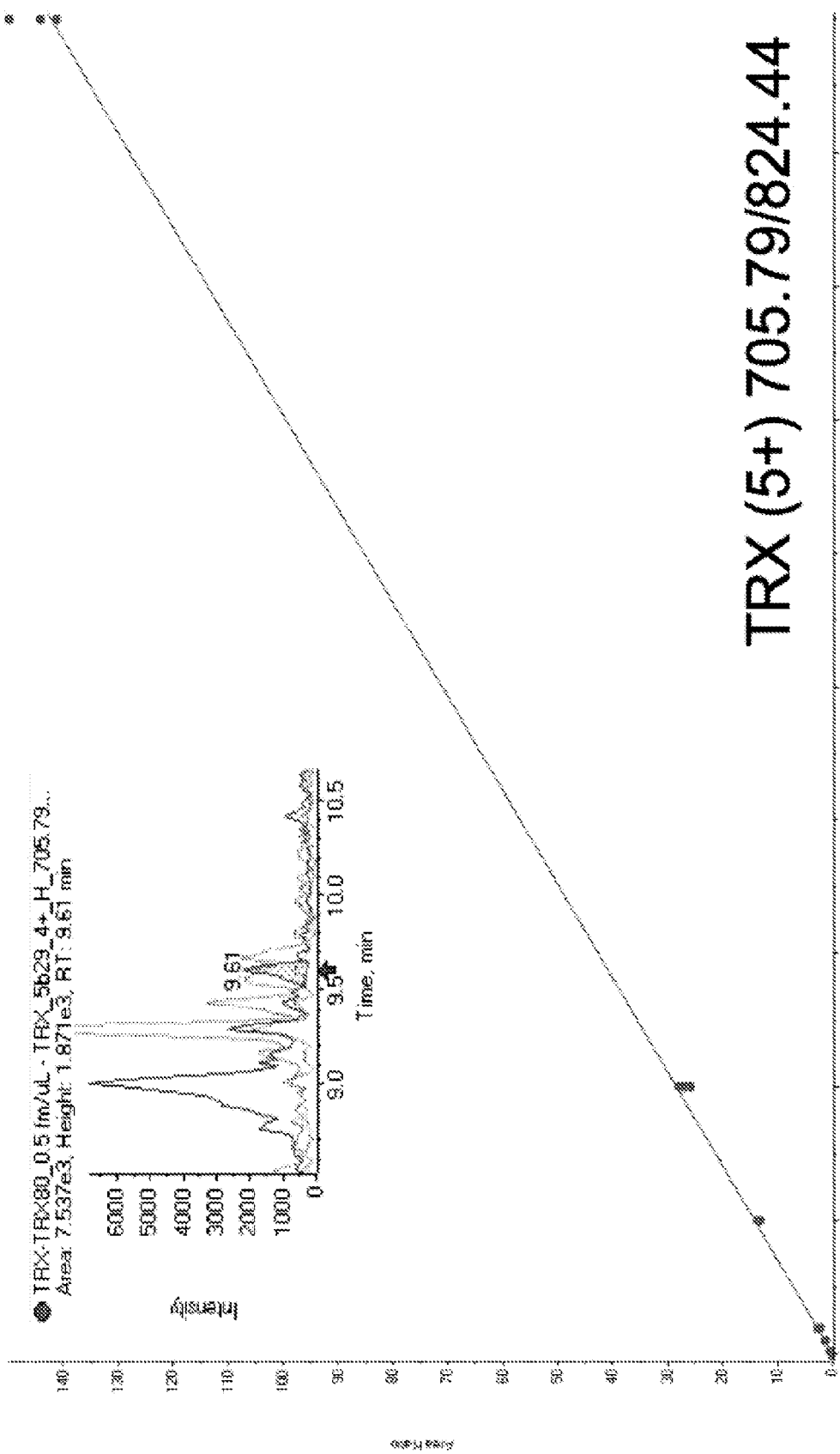
Figure 3D:
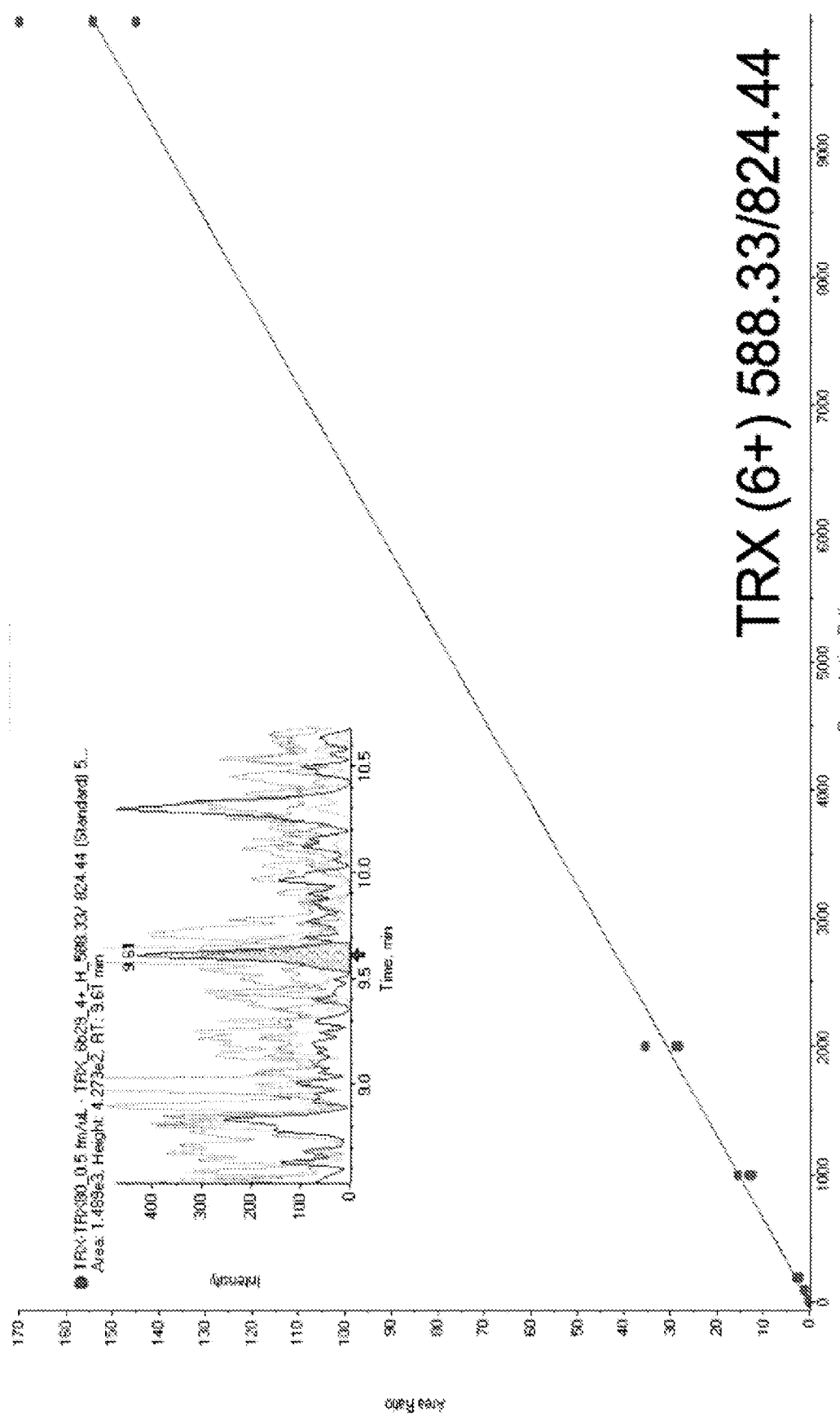

The present inventors describe herein a method in which samples (e.g. plasma or CSF) are digested (e.g. chemically digested using cyanogen bromide (CNBr)), resulting in the production of unique, identifying peptides for TRX and for TRX 80. Methods such as mass spectrometry analysis then can be used for the detection and quantitation of these peptides after digestion of a complex sample, eliminating the problems of antibody cross reaction, the necessity of available conformational epitopes for detection, and complications due to protein-protein interactions. The inventors detail a process of assay development to detect these proteins at biologically relevant levels, beginning with validating the chemical digestion protocol and examining the limits of detection for these peptides by MALDI in conjunction with various sample fractionation methods. In addition, they describe the development of a sensitive MRM assay for consistent, accurate quantitation of TRX and TRX 80 that has applications for research and clinical samples.

One aspect of the invention is a method for detecting a full-length protein and a truncated form (e.g., a naturally occurring cleavage product) thereof, in a sample, comprising
optionally denaturing and/or reducing proteins in the sample,
cleaving the proteins into smaller peptides, and
detecting a unique peptide identifier for the full-length protein and/or a unique peptide identifier for the truncated protein, in the sample.

In embodiments of this method, proteins in the sample are cleaved by chemical cleavage (e.g., cleavage at aspartyl residues by formic acid, cyanogen bromide cleavage, or 2-iodosobenzoic acid cleavage (IBA)) or with a protease (e.g., trypsin, chymotrypsin, or Lys-C). The chemical or enzymatic agents that are selected to cleave a protein of interest is a function of, for example, the sequence of the protein to be cleaved. The choice of an appropriate cleavage agent will be evident to a skilled worker. The agents indicated above are all useful for the cleavage of TRX and its variants. In embodiments of the invention, the N-terminal peptides from the full-length and the truncated protein are different, and can serve as unique peptide identifiers for the two proteins; or the C-terminal peptides from the full-length and the truncated protein are different, and can serve as unique peptide identifiers for the two proteins.

In one embodiment of the invention, the full-length protein is thioredoxin (TRX), and the truncated form thereof is its biologically active, C-terminal truncated, 10 kDa cleavage product, TRX 80. In this embodiment, the unique peptide identifier for TRX can be PTFQFFKKGQKVGEFS-GANKEKLEATINELV (SEQ ID NO:1), and the unique peptide identifier for TRX 80 can be PTFQFFK (SEQ ID NO:2). In this method, the proteins in the sample are optionally denatured and reduced. The need for denaturation and/or reduction is a function of the type of cleavage being carried out. For example, denaturation is required for CNBr cleavage, but not for digestion with trypsin. It will be evident to a skilled worker if denaturation and/or reduction is required for a particular cleavage method. The proteins are then cleaved by chemical cleavage (e.g., as described above) or with a protease (e.g., as described above); the C-terminal peptides from the full-length and the truncated protein are different, and can serve as unique peptide identifiers for the two forms of the protein. In one embodiment, the proteins in the sample are denatured and reduced and are then cleaved with cyanogen bromide, to produce, among other peptides common to the two forms of the protein, the unique peptide identifiers represented by SEQ ID NO:1 and SEQ ID NO:2.

In methods of the invention, the unique peptide identifiers can be detected by any of a variety of methods, including HPLC, ELISA, electrochemiluminescence, flow cytometry based bead assays, mass spectrometry (MS), a multiple reaction monitoring assay (MRM), or selective reaction monitoring assay (SRM).

The detection step in a method of the invention can be quantitative.

The sample used in a method of the invention can be, e.g., a cell homogenate, a tissue homogenate, a biopsy tissue homogenate, serum/plasma, cerebrospinal fluid (CSF), synovial fluid, urine, cardiac tissue, tears, saliva, or culture medium in which cells have been grown.

Another aspect of the invention is an antibody that is specific for a contiguous sequence of between 5 and 7 amino acids that is shared by the peptides represented by SEQ ID NO:1 and SEQ ID NO:2. In one embodiment of the invention, the antibody is specific for the sequence, PTFQFFK (SEQ ID NO:2).

Another aspect of the invention is a composition comprising a) an antibody specific for the peptide represented by SEQ ID NO:1, and/or b) an antibody specific for the peptide represented by SEQ ID NO:2, and/or c) an antibody specific for a peptide represented by a contiguous sequence of between 5 and 7 amino acids that is shared by SEQ ID NO:1 and SEQ ID NO:2.

Another aspect of the invention is a method for diagnosing a disease or condition in a subject, wherein the disease or condition is characterized by a level of TRX and/or TRX 80 that is altered by a statistically significant value compared to a control (e.g., a value that is proportional to the level in a subject that does not exhibit symptoms of the disease or condition), the method comprising detecting the presence and/or amounts of TRX and TRX 80 in a sample from the subject by the a method of the invention.

Another aspect of the invention is a kit for performing one of the methods of the invention. The kit can comprise, e.g., antibodies that are specific for one or more unique identifying peptides for distinguishing between two or more forms of one protein, or one or more unique identifying peptides for distinguishing between variants of more than one protein. A kit of the invention can be used, e.g., for pre-processing a sample for analysis by a method of the invention.

Any of a variety of proteins and variants thereof can be distinguished from one another by a method of the invention, provided that cleavage of a protein and a variant thereof results in at least one peptide that is unique to the protein (a unique peptide identifier for the protein) and at least one peptide that is unique to the variant (a unique peptide identifier for the truncated variant). As used herein, the terms "a," "an," and "the" include plural referents unless the context clearly dictates otherwise. For example, as used above, more than one protein can be analyzed simultaneously by a method of the invention, and more than one variant can be distinguished for each of the proteins.

For example, a protein can be distinguished from a form of the protein that is truncated at its N-terminus and/or at its C-terminus. In a method of the invention, proteins in a sample are cleaved (e.g., digested) into smaller peptides. Cleavage conditions are selected so that, in addition to peptides that are in common between the protein and its variant, one or more peptides are generated that are unique to each form of the protein. In one embodiment of the invention, in which a full-length protein and a C-terminal truncated form thereof are distinguished, a sample comprising both forms of the protein is treated with a cleavage agent so that the C-terminal peptide of the full-length protein is longer than the C-terminal peptide of the truncated form.

A "unique peptide identifier" for a particular protein, as used herein, refers to a peptide which, following cleavage of the proteins in a sample, is generated from the particular protein, but not from a variant of that protein which an investigator wishes to distinguish from the particular protein, and which thus can be used to identify that protein. Furthermore, the unique peptide identifier must not be common to other cleaved proteins in the sample, which can comprise a complex mixture of proteins. For example, if the proteins of interest are in a human sample, the unique peptide identifier must not be generated by digestion of any other protein in that human sample. An investigator can insure that a peptide identifier is not present in other proteins in the sample being analyzed by performing a conventional BLAST analysis of the peptide identifier against, e.g., all known human proteins.

In another embodiment of the invention, instead of distinguishing a C-terminal truncated form of a protein from a version of the protein that is not truncated at its C-terminus, an N-terminal truncated form of a protein is distinguished from a version of the protein that is not truncated at its N-terminus. In this embodiment, the peptide from the N-terminus of the truncated protein is shorter than the N-terminal peptide of the non-truncated protein.

In other embodiments of the invention, proteins that differ from one another by internal sequences in the protein can be distinguished. For example, unique peptide identifiers can be used which correspond to internal deletions, or even single amino acid changes, within a variant form of the protein.

Much of the description herein is directed to the detection of the full-length form of TRX and of the truncated form thereof referred to as TRX 80, which is a biologically active cleavage form of TRX, having a molecular weight of 10 kDa and a truncation at the C-terminal end. However, it will be evident to a skilled worker that any pair (or set) of suitable proteins can be distinguished by a method of the invention. The description herein thus applies to such other pairs (or sets) of proteins, as well.

Furthermore, the naturally truncated form of TRX (TRX 80) that is discussed herein is the human form of the processed protein. However, the TRX protein can be differentially processed in other biological systems. Therefore, among the cleaved forms of TRX (e.g., in the form of isolated peptides) that can be identified by a method of the invention are:

| | |
|---|---|
| PTFQFFKKGQKVGEFSGANKEKLEATINELV | (SEQ ID NO: 7) |
| PTFQFFKKGQKVGEFSGANKEKLEATINEL | (SEQ ID NO: 8) |
| PTFQFFKKGQKVGEFSGANKEKLEATINE | (SEQ ID NO: 9) |
| PTFQFFKKGQKVGEFSGANKEKLEATIN | (SEQ ID NO: 10) |
| PTFQFFKKGQKVGEFSGANKEKLEATI | (SEQ ID NO: 11) |
| PTFQFFKKGQKVGEFSGANKEKLEAT | (SEQ ID NO: 12) |
| PTFQFFKKGQKVGEFSGANKEKLEA | (SEQ ID NO: 13) |
| PTFQFFKKGQKVGEFSGANKEKLE | (SEQ ID NO: 14) |
| PTFQFFKKGQKVGEFSGANKEKL | (SEQ ID NO: 15) |
| PTFQFFKKGQKVGEFSGANKEK | (SEQ ID NO: 16) |
| PTFQFFKKGQKVGEFSGANKE | (SEQ ID NO: 17) |
| PTFQFFKKGQKVGEFSGANK | (SEQ ID NO: 18) |
| PTFQFFKKGQKVGEFSGAN | (SEQ ID NO: 19) |
| PTFQFFKKGQKVGEFSGA | (SEQ ID NO: 20) |
| PTFQFFKKGQKVGEFSG | (SEQ ID NO: 21) |
| PTFQFFKKGQKVGEFS | (SEQ ID NO: 22) |
| PTFQFFKKGQKVGEF | (SEQ ID NO: 23) |
| PTFQFFKKGQKVGE | (SEQ ID NO: 24) |
| PTFQFFKKGQKVG | (SEQ ID NO: 25) |
| PTFQFFKKGQKV | (SEQ ID NO: 26) |
| PTFQFFKKGQK | (SEQ ID NO: 27) |
| PTFQFFKKGQ | (SEQ ID NO: 28) |
| PTFQFFKKG | (SEQ ID NO: 29) |
| PTFQFFKK | (SEQ ID NO: 30) |
| PTFQF | (SEQ ID NO: 31) |

A skilled worker will be able to identify which of the above forms of the peptides are present in a given biological system. A unique peptide identifier for TRX or a C-terminal deletion thereof can be any contiguous sequence from the N-terminus of the peptide beginning with PTFQ (SEQ ID NO:32) up to the full length of SEQ ID NO:1 without the C terminal valine (V).

Further, while the sequences above are specific to the mammalian form of TRX and TRX80, this method may be applied to other homologues of TRX and TRX80 in other species. A skilled worker would be able to identify which homologues or orthologues of TRX and TRX80 are present in an alternative species by using conventional BLAST comparisons.

The levels of TRX and/or TRX 80 appear to be a link between oxidative stress and inflammation. An assay capable of quantitating both the full-length and truncated forms of TRX is highly valuable. The present inventors describe herein an exemplary assay for distinguishing between, and quantitating, these two forms of the TRX protein, using both LC-MALDI and multiple reaction monitoring (MRM) mass spectrometry-based assays, in which digestion of samples with cyanogen bromide (CNBr) results in unique identifying peptides for both TRX and TRX 80 that can be quantitated in complex samples, including plasma. These methods overcome limitations of antibody-based detection methods that are imposed by the properties of TRX and TRX 80.

Samples to be analyzed by a method of the invention can originate from a variety of biological sources, including, e.g., humans or other animals, plants, viruses, etc. A variety of types of cells, tissues, organelles etc. can serve as sources for samples for a method of the invention. These include, e.g., serum/plasma, cerebral spinal fluid (CSF), synovial fluid, cell homogenates, tissue homogenates, urine, cardiac tissue, tears, saliva, biopsy tissues or the like.

A variety of conventional methods can be used to cleave proteins in a method of the invention. A cleavage method is selected which results in peptides, particularly unique peptide identifiers, that are of a size that can be readily resolved by the detection method to be used. For example, when mass spectrometry is used to analyze the resulting peptides, a cleavage method is selected which results in peptide fragments in an observable mass range for tandem MS mass spectrometers (about 500-about 7000 DA). When the peptides are detected by contact with an antibody, they should be of a size that is amenable to antibody binding. Such peptides can be, e.g., at least about 5-8 amino acids in length, e.g. about 5-20, or more, amino acids, or about 8-15 amino acids. As used herein, the term "about" refers to plus or minus 10%. For example, "about 8 amino acids" is 7-9 amino acids. A "range" of values, as used herein, includes the end points of the range. Thus, for example, 5-7 includes both 5 and 7.

In one embodiment of the invention, well-known chemical cleavage methods are employed, such as cleavage at aspartyl residues by formic acid, cyanogen bromide cleavage, 2-iodosobenzoic acid cleavage (IBA, e.g. using 2-Nitro-5-thiocyanatobenzoic acid powder), BNPS-Skatole cleavage, hydroxylamine cleavage, etc.

In another embodiment, a protease, generally a site-specific protease, or a combination of such proteases, is used. The proteases can be selected from, e.g., serine proteases, threonine proteases, cysteine proteases, aspartic acid proteases (e.g., plasmepsis), metailoproteases, glutamic acid proteases, or combinations thereof. Suitable proteases include, e.g., the proteases shown in Table 1.

TABLE 1

Achromopeptidase
Aminopeptidase
Ancrod
Angiotensin Converting Enzyme
Arg-C proteinase
Asp-N endopeptidase
Asp-N endopeptidase + N-terminal Glu
Bromelain
Calpain
Calpain I
Calpain II
Carboxypeptidase A
Carboxypeptidase B
Carboxypeptidase G
Carboxypeptidase P
Carboxypeptidase W
Carboxypeptidase Y
Caspase
Caspase 1
Caspase 2
Caspase 3

TABLE 1-continued

Caspase 4
Caspase 5
Caspase 6
Caspase 7
Caspase 8
Caspase 9
Caspase 10
Caspase 13
Cathepsin B
Cathepsin C
Cathepsin D
Cathepsin G
Cathepsin H
Cathepsin L
Chymopapain
Chymase
Chymotrypsin - high specificity (C-term to FYW], not before P
Chymotrypsin - low specificity (C-term to FYWML (SEQ ID NO: 33)], not before P
Clostripain (Clostriiopeptidase B)
Collagenase
Complement C1r
Complement C1s
Complement Factor D
Complement factor I
Cucumisin
Dipeptidyl Peptidase IV
Elastase, leukocyte
Elastase, pancreatic
Endoproteinase Arg-C
Endoproteinase Asp-N
Endoproteinase Glu-C
Endoproteinase Lys-C
Enterokinase
Factor Xa
Ficin
Furin
Glutamyl endopeptidase
Granzyme A
Granzyme B
HIV Protease
IGase
Kallikrein tissue
Leucine Aminopeptidase (General)
Leucine aminopeptidase, cytosol
Leucine aminopeptidase microsomal
LysN
Matrix metalloprotease
Methionine Aminopeptidase
Neutrase
Papain
Pepsin (pH 1.3)
Pepsin (pH > 2)
Plasmin
Prolidase
Pronase E
Prostate Specific Antigen
Protease, Alkalophilic from *Streptomyces griseus*
Protease from *Aspergillus*
Protease from *Aspergillus saitoi*
Protease from *Aspergillus sojae*
Protease (*B. licheniformis*) (Alkaline)
Protease (*B. licheniformis*) (Alcalase)
Protease from *Bacillus* polymyxa
Protease from *Bacillus* sp
Protease from *Bacillus* sp (Esperase)
Protease from *Rhizopus* sp.
Protease S
Proteasomes
Proteinase from *Aspergillus oryzae*
Proteinase 3
Proteinase A
Proteinase K
Protein C
Pyroglutamate aminopeptidase
Renin
Rennin
Staphylococcal peptidase I
Streptokinase
Subtilisin
Thermolysin
Thrombin
Tissue Plasminogen Activator
Tobacco etch virus protease
Trypsin
Tryptase
Urokinase Among the commonly used proteases are: Endoproteinase Asp-N from a *Pseudomonas fragi* mutant; Endoproteinase Glu-C from *Staphylococcus aureus* V8; Endoproteinase Glu-C from *Staphylococcus aureus* V8; Endoproteinase Lys-C from *Lysobacter enzymogenes*; Endoproteinase Pro-C from *E. coli* BioChemika; Endoproteinase Pro-Pro-Y-Pro; Papain; Pepsin; Proteinase A (e.g. from *S. cerevisiae*); Proteinase K; Proteinase from *Bacillus licheniformis* Type VIII; α-Chymotrypsin; and Trypsin. See, e.g., the Sigma-Aldrich catalogue.

Combinations of chemical and protease methods of cleavage can also be used.

In some embodiments, proteins in a sample are denatured and/or reduced before they are cleaved. These procedures may be necessary for exposing desired cleavage sites to a cleavage agent, and/or for eliminating problems resulting from protein-protein interactions (either aggregation or, e.g., dimer formation of a particular protein, or interactions of a protein of interest with other proteins in the sample). A skilled worker will recognize in what situations denaturation and/or reduction of proteins in a sample may be beneficial. When quantitation of one or both unique peptide identifiers is performed, it is preferable that the cleavage (e.g., protease digestion or chemical cleavage) is carried out to completion.

A variety of types of methods can be used to detect unique peptide identifiers in a sample. The detection may be quantitative. For example, the peptides can be detected mass spectrometry. (sometimes abbreviated herein as "mass spec"). Among the many suitable detection methods are, e.g., HPLC; Western blotting (immunoblotting); ELISA; isoelectric focusing followed by Western blotting ELISA, or mass spec of fractions; antibody selection followed by immunological detection or mass spec (MS); matrix-assisted laser desorption/ionization spectroscopy (MALDI, or LC-MALDI); surface-enhanced laser desorption/ionization (SELDI), electrospray ionization mass spectroscopy (ESI); TOF; quadrupole; ion trap; orbitotrap mass analyzers and various configurations of these (e.g., triple quad, etc); a multiple reaction monitoring assay (MRM); selective reaction monitoring assay (SRM); and multiple reaction monitoring (MRM).

In one embodiment of the invention, mass spectrometry is used. Among the variety of methods of mass spectral analysis that can be employed, which use different forms of ionization, are, e.g., electron ionization, chemical ionization (CI), electrospray ionization (ESI), matrix-assisted laser desorption/ionization (MALDI), inductively coupled plasma (ICP), glow discharge, fast atom bombardment (FAB), thermospray, desorption/ionization on silicon (DIOS), direct analysis in real time (DART), atmospheric pressure chemical ionization (APCI), secondary ion mass spectrometry (SIMS), thermal ionization, nanospray, corona discharge, atmospheric pressure MALDI (AP-MALDI), desorption electrospray ionization (DESI), and chemical ionization (CI).

It will be evident to a skilled worker that a variety of methods of mass spectral analysis can be performed, using different forms of ionization. These include, e.g., electron ionization and chemical ionization for gases and vapors, and electrospray ionization (ESI) and matrix-assisted laser desorption/ionization (MALDI) for liquid and solid biological samples. A variety of sources can be used, including inductively coupled plasma sources, glow discharge, fast atom bombardment (FAB), thermospray, desorption/ionization on silicon (DIOS), direct analysis in real time (DART), atmospheric pressure chemical ionization (APCI), secondary ion mass spectrometry (SIMS), thermal ionization, nanospray, corona discharge, atmospheric pressure MALDI (AP-MALDI), desorption electrospray ionization (DESI), chemical ionization (CI) and inductively coupled plasma (ICP). Different sources of ionization can give rise to analytes (e.g. peptides) having different charges. For example, in ESI, peptides often exhibit multiple charges (e.g. +2H, +3H); whereas in MALDI, peptides almost exclusively have only a single charge. The manner in which analytes (e.g. peptides) receive their charge has an effect on the peptides that are observed. Some peptides ionize better by one method than the other, and vice versa. There is not 100% overlap between what is observed in MALDI vs. what is observed in ESI. In some cases, a peptide identified as being highly ionizing by one of these methods may not be observed with the other method. Therefore, it may be necessary in some cases to use antibodies against different peptides for MALDI as for ESI applications. However, because there is some overlap between targets identified by the ESI and MALDI methods, it may in some cases be possible to use the same antibodies for both MALDI and ESI applications. A skilled worker can readily determine which peptides (and antibodies thereto) are suitable for use for which type of ionization procedure. A method of the invention can be used to identify thioredoxin peptides for a variety of types of ionization, and a variety of types of mass spectrometry.

The detection (identification and, optionally, quantitation) of full-length thioredoxin (TRX) and/or its truncated product (TRX 80) can be used for laboratory assays or for clinical assays, in the context of many diseases, as well as general health. It can also be used for laboratory animal research or in the context of veterinary medicine. Clinically, TRX and/or TRX 80 may be diagnostic markers of disease on their own, or in combination with other markers. Varying ratios of the amount of TRX to its truncated form of TRX 80 in biological systems can also constitute valuable markers of disease processes.

The level of TRX is increased in the context of many disease processes, examples of which are well-known to those of skill in the art. Elevated levels appear to be a general marker of oxidative stress. Oxidative stress can lead to the increased expression and secretion of TRX, which then can be cleaved by monocyctes into a 10 kDa product, TRX 80. TRX 80 possesses monocyte chemoattractant activity, inducing monocyte differentiation and activation into a highly inflammatory phenotype termed the TRX80 activated monocyte (TAM). TRX 80 is detected at highly variable plasma levels of presumed healthy donors and has been implicated in rheumatoid arthritis. Levels of TRX/TRX80 appear to be a link between oxidative stress and inflammation.

Increased plasma levels of TRX have been demonstrated in many disease conditions, including, e.g., heart failure, cardiomyopathy, cancer, asthma, and rheumatoid arthritis, among others. Further, the ratio of amounts of TRX/TRX80 have been shown to be correlated with certain disease conditions, and with the progress of those conditions. Thus, tracking levels of TRX and/or TRX 80 can serve as a therapeutic or diagnostic marker for a variety of disease conditions, provide a valuable clinical assay for monitoring disease progression in many conditions, and aid in evaluating the efficacy of therapeutic interventions for certain diseases. Such assays can be used in conjunction with other diagnostic methods, including the detection of other biomarkers, for the disease state being analyzed.

In general, when performing a diagnostic assay for a disease condition in a subject, an investigator compares the levels of TRX and/or TRX 80 in the subject to a control value or negative reference standard (e.g. a level proportional to that in a subject that does not express symptoms of the disease condition). A value of TRX and/or TRX80 that is statistically significantly higher (or in some cases, lower) than that of the control is indicative of the presence of the disease condition. If desired, a positive reference standard, which correlates with the presence of the disease condition, can be used instead of, or in addition to, the negative standard. A "significantly" elevated or decreased level of TRX and/or TRX 80 (compared to a reference standard) is a level whose difference from the value of the reference standard is statistically significant, using statistical methods that are appropriate and well-known in the art, generally with a probability value of less than five percent chance of the change being due to random variation.

Using samples from subjects as a clinical diagnostic reference standard is generally not practical on a routine basis. Instead, one way to generate negative and positive reference standards is to use lysates from cells in culture, and establish a cut-point value by a direct comparison of the cell culture lysates to a true positive and true negative. Alternatively, reference standards (values) obtained from accumulated data or databases (e.g. published by others) can be used.

Exemplary disease conditions for which TRX appears to be a biomarker are shown in Table 2:

TABLE 2

Conditions in which thioredoxin has been proposed to play a role or is a biomarker (partial list)

| Disease/context | Thioredoxin: | References |
| --- | --- | --- |
| Alzheimer's | Decreased TRX levels in patient brains<br>TRX80 not examined | (Lovell et al, 2000) |
| Rheumatoid Arthritis | TRX80 Secreted by synovial cells in RA<br>Elevated TRX levels in synovial fluid correlate with inflammation | (Lemarechal et al, 2007)<br>(Maurice et al, 1999) |
| Atherosclerosis | Increased plasma levels<br>Increased expression in endothelial cells and macrophages in plaques<br>Role in pathogenesis is debated<br>TRX80 not examined | (Miyamoto et al, 2005)<br>(Takagi et al, 1998) |

TABLE 2-continued

Conditions in which thioredoxin has been proposed to play a role or is a biomarker (partial list)

| Disease/context | Thioredoxin: | References |
|---|---|---|
| Asthma | Elevated serum TRX<br>Application of exogenous TRX may ameliorate oxidative stress in pulmonary inflammation<br>TRX80 not examined | (Yamada et al, 2003)<br>(Ichiki et al, 2005) |
| Cancer | Over-expression of TRX in many solid tumors<br>High levels of TRX in chemotherapy resistant tumors<br>Secretion of TRX from neoplastic cells<br>PX-12 Thioredoxin inhibitor is in clinical trials for therapy<br>TRX80 not examined | (Grogan et al, 2000)<br>(Yamada et al, 1996)<br>(Shao et al, 2001)<br>(Jordan et al, 2005) |
| Cardiac Hypertrophy | Protective antioxidant properties of TRX<br>Also role of TRX as a growth factor, contributing to hypertrophy<br>TRX80 not examined | (Ago and Sadoshima, 2007)<br>(Yamamoto et al, 2003) (Sadoshima et al, 2007) |
| Diabetes | Increased plasma TRX levels<br>SNP in TXN UTR associated with susceptibility to Type I diabetes<br>TXNIP, inhibitor of TRX, is upregulated in diabetes<br>TRX80 not examined | (Miyamoto et al, 2005) (Ikegami et al, 2008) (Schulze et al, 2004) |
| HIV | Increased plasma levels of TRX<br>Increased TRX levels in bone marrow<br>Depletion of TRX positive cells in lymph nodes<br>TRX reductase suppresses TAT dependent HIV transcription<br>TRX80 associated with elevated HIV replication in Mφ in culture | (Nakamura et al, 1996)<br>(Van Laer et al, 2002) (Masutani et al, 1992) (Kalantari et al, 2008) (Newman et al, 1994) |
| Hypertension | Different models suggest increases or decreases in expression<br>Decreased TRX expression in myocardium<br>TRX80 not examined | (Ebrahimian and Touyz, 2008)<br>(Tanito et al, 2004) |
| Ischemia-Reperfusion | Exogenous TRX or TRX over-expression is protective<br>Increased TRX expression is seen in the brain with ischemia<br>TRX80 not examined | (Okubo et al, 1997)<br>(Takagi et al, 1998)<br>(Tao et al, 2006) |
| Malaria | TRX system is essential for parasite to survive host immune defense, TRX reductase has been target for potential inhibitors<br>TRX80 not examined | (Becker et al, 2004) |
| HBV, HTLV-1, HCV | Elevated TRX serum levels<br>TRX80 not examined | (Sumida et al, 2000)<br>(Masutani et al, 2005) |

Ago T, Sadoshima J (2007). Thioredoxin) as a negative regulator of cardiac hypertrophy. *Antioxid Redox Signal* 9: 679-87.

Becker K, Tilley L, Vennerstrom J L, Roberts D, Rogerson S, Ginsburg H (2004). Oxidative stress in malaria parasite-infected erythrocytes: host-parasite interactions. *Int J Parasitol* 34: 163-89.

Ebrahimian T, Touyz R M (2008). Thioredoxin in vascular biology: role in hypertension. *Antioxid Redox Signal* 10: 1127-36.

Grogan T M, Fenoglio-Prieser C, Zeheb R, Bellamy W, Frutiger Y, Vela E, Stemmerman G, Macdonald J, Richter L, Gallegos A, Powis G (2000). Thioredoxin, a putative oncogene product, is overexpressed in gastric carcinoma and associated with increased proliferation and increased cell survival. *Hum Pathol* 31: 475-81.

Ichiki H, Hoshino T, Kinoshita T, Imaoka H, Kato S, Inoue H, Nakamura H, Yodoi J, Young H A, Aizawa H (2005). Thioredoxin suppresses airway hyperresponsiveness and airway inflammation in asthma. *Biochem Biophys Res Commun* 334: 1141-8.

Ikegami H, Ono M, Fujisawa T, Hiromine Y, Kawabata Y, Yamato E (2008). Molecular scanning of the gene for thioredoxin, an antioxidative and antiapoptotic protein, and genetic susceptibility to type 1 diabetes. *Ann N Y Acad Sci* 1150: 103-5.

Jordan B F, Runquist M, Raghunand N, Gillies R J, Tate W R, Powis G, Baker A F (2005). The thioredoxin-1 inhibitor 1-methylpropyl 2-imidazolyl disulfide (PX-12) decreases vascular permeability in tumor xenografts monitored by dynamic contrast enhanced magnetic resonance imaging. *Clin Cancer Res* 11: 529-36.

Kalantari P, Narayan V, Natarajan S K, Muralidhar K, Gandhi U H, Vunta H, Henderson A J, Prabhu K S (2008). Thioredoxin reductase-1 negatively regulates HIV-1 transactivating protein Tat-dependent transcription in human macrophages. *J Biol Chem* 283: 33183-90.

Lemarechal H, Anract P, Beaudeux J L, Bonnefont-Rousselot D, Ekindjian O G, Borderie D (2007). Expression and extracellular release of Trx80, the truncated form of thioredoxin, by TNF-alpha- and IL-1beta-stimulated human synoviocytes from patients with rheumatoid arthritis. *Clin Sci (Loud)* 113: 149-55.

Lovell M A, Xie C, Gabbita S P, Markesbery W R (2000). Decreased thioredoxin and increased thioredoxin reductase levels in Alzheimer's disease brain. *Free Radic Biol Med* 28: 418-27.

Masutani H, Naito M, Takahashi K, Hattori T, Koito A, Takatsuki K, Go T, Nakamura H, Fujii S, Yoshida Y, et al. (1992). Dysregulation of adult T-cell leukemia-derived factor (ADF)/thioredoxin in HIV infection: loss of ADF high-producer cells in lymphoid tissues of AIDS patients. *AIDS Res Hum Retroviruses* 8: 1707-15.

Masutani H, Ueda S, Yodoi J (2005). The thioredoxin system in retroviral infection and apoptosis. *Cell Death Differ* 12 Suppl 1: 991-8.

Maurice M M, Nakamura H, Gringhuis S, Okamoto T, Yoshida S, Kullmann F, Lechner S, van der Voort E A, Leow A, Versendaal J, Muller-Ladner U, Yodoi J, Tak P P, Breedveld F C, Verweij C L (1999). Expression of the thioredoxin-thioredoxin reductase system in the inflamed joints of patients with rheumatoid arthritis. *Arthritis Rheum* 42: 2430-9.

Miyamoto S, Kawano H, Hokamaki J, Soejima H, Kojima S, Kudoh T, Nagayoshi Y, Sugiyama S, Sakamoto T, Yoshimura M, Nakamura H, Yodoi J, Ogawa H (2005). Increased plasma levels of thioredoxin in patients with glucose intolerance. *Intern Med* 44: 1127-32.

Nakamura H, De Rosa S, Roederer M, Anderson M T, Dubs J G, Yodoi J, Holmgren A, Herzenberg L A, Herzenberg L A (1996). Elevation of plasma thioredoxin levels in HIV-infected individuals. *Int Immunol* 8: 603-11.

Newman G W, Balcewicz-Sablinska M K, Guarnaccia J R, Remold H G, Silberstein D S (1994). Opposing regulatory effects of thioredoxin and eosinophil cytotoxicity-enhancing factor on the development of human immunodeficiency virus 1. *J Exp Med* 180: 359-63.

Okubo K, Kosaka S, Isowa N, Hirata T, Hitomi S, Yodoi J, Nakano M, Wada H (1997). Amelioration of ischemia-reperfusion injury by human thioredoxin in rabbit lung. *J Thorac Cardiovasc Surg* 113: 1-9.

Schulze P C, Yoshioka J, Takahashi T, He Z, King G L, Lee R T (2004). Hyperglycemia promotes oxidative stress through inhibition of thioredoxin function by thioredoxin-interacting protein. *J Biol Chem* 279: 30369-74.

Shao L, Diccianni M B, Tanaka T, Gribi R, Yu A L, Pullen J D, Camitta B M, Yu J (2001). Thioredoxin expression in primary T-cell acute lymphoblastic leukemia and its therapeutic implication. *Cancer Res* 61: 7333-8.

Sumida Y, Nakashima T, Yoh T, Nakajima Y, Ishikawa H, Mitsuyoshi H, Sakamoto Y, Okanoue T, Kashima K, Nakamura H, Yodoi J (2000). Serum thioredoxin levels as an indicator of oxidative stress in patients with hepatitis C virus infection. *J Hepatol* 33: 616-22.

Takagi Y, Gon Y, Todaka T, Nozaki K, Nishiyama A, Sono H, Hashimoto N, Kikuchi H, Yodoi J (1998). Expression of thioredoxin is enhanced in atherosclerotic plaques and during neointima formation in rat arteries. *Lab Invest* 78: 957-66.

Tanito M, Nakamura H, Kwon Y W, Teratani A, Masutani H, Shioji K, Kishimoto C, Ohira A, Horie R, Yodoi J (2004). Enhanced oxidative stress and impaired thioredoxin expression in spontaneously hypertensive rats. *Antioxid Redox Signal* 6: 89-97.

Tao L, Gao E, Hu A, Coletti C, Wang Y, Christopher T A, Lopez B L, Koch W, Ma X L (2006). Thioredoxin reduces post-ischemic myocardial apoptosis by reducing oxidative/nitrative stress. *Br J Pharmacol* 149: 311-8.

Van Laer A, Dallalio G, McKenzie S W, Means R T, Jr. (2002). Thioredoxin and protein nitrotyrosine in bone marrow supernatant from patients with human immunodeficiency virus infection. *J Investig Med* 50: 10-8.

Yamada M, Tomida A, Yoshikawa H, Taketani Y, Tsuruo T (1996). Increased expression of thioredoxin/adult T-cell leukemia-derived factor in cisplatin-resistant human cancer cell lines. *Clin Cancer Res* 2: 427-32.

Yamada Y, Nakamura H, Adachi T, Sannohe S, Oyamada H, Kayaba H, Yodoi J, Chihara J (2003). Elevated serum levels of thioredoxin in patients with acute exacerbation of asthma. *Immunol Lett* 86: 199-205.

Yamamoto M, Yang G, Hong C, Liu J, Holle E, Yu X, Wagner T, Vatner S F, Sadoshima J (2003) Inhibition of endogenous thioredoxin in the heart increases oxidative stress and cardiac hypertrophy. *J Clin Invest* 112: 1395-406.

In one embodiment of the invention, in which the sample is plasma, a specific CNBr cleaved peptide from hemoglobin can also be tracked and quantitated to indicate levels of hemolysis in the sample. This type of analysis can be useful for the development of a correction for the contribution of TRX by hemolysis, which can be an important consideration.

In one embodiment of the invention, an antibody is produced which is specific for a common region of the two unique TRX peptides discussed herein (e.g., PTFQFFK (SEQ ID NO:2), or a shorter version, such as a 5-6 amino acid version, of this sequence). This antibody can be used, e.g., for detection of the peptides, or to develop an affinity capture platform which would allow for the enrichment of these peptides prior to later detection methods such as mass spectrometry. Using such antibodies in this manner can readily allow for the simplification of sample peptide mixtures and the subsequent detection of TRX and TRX 80 at very low concentrations in samples of highly diverse protein composition. One of the key challenges in current mass spectrometry methods is that as sample complexity is increased, the ability to detect specific analytes (here two unique peptides) may be decreased. Currently, affinity based methods are often employed to reduce sample complexity by depleting samples such as plasma of high abundance proteins such as albumin. However, TRX can be found associated with albumin, and this would also deplete TRX from the samples. Thus, the ability to pre-process complete samples by chemical digestion, and to then affinity target the desired unique identifying peptides without concerns of protein interactions allows added efficiency of detection of the proteins at low levels.

The production of such an antibody can also enable the use of this digestion method in conjunction with gel based applications involving separation of the peptides based on size or isoelectric point followed by antibody based detection (e.g. immunoblotting), but with the elimination of the problems associated with protein interactions in samples, masking of epitopes, or the requirement for native conformation.

In addition, this method can be expanded to also include evaluation of protein modifications occurring on the unique or shared peptides of TRX and TRX 80 after digestion. This includes examination of the modification of the active site cysteines in the protein with oxidation, disulfide bond formation, nitrosylation or other mechanisms, and also such changes to other residues of the proteins, including cysteine modifications outside of the active site. These modifications can be detected with the use of mass spectrometry or an antibody raised to the specific modification.

An antibody that is "specific for" a peptide refers to an antibody that preferentially recognizes a defined sequence of amino acids, or epitope, that is present in the peptide, and not generally other peptides unintended for binding to the antibody. An antibody that "binds specifically" to ("is specific for"; binds "preferentially" to) a peptide of the invention interacts with the antibody, or forms or undergoes a physical association with it, in an amount and for a sufficient time to allow, e.g., the peptide to be removed from the solution, or to be captured from the solution, in conjunction with a method of the invention. By "specifically" or "preferentially" is meant that the antibody has a higher affinity, e.g. a higher degree of selectivity, for such a peptide than for other peptides in a sample. For example, the antibody can have an affinity for the peptide of at least about 5-fold higher than for other peptides in the sample. Typically this is application specific. For example, it does not matter if the antibody cross-reacts with peptides from proteins of different samples, if those peptides are not present in the sample of interest. The affinity or degree of specificity can be determined by a variety of routine procedures, including, e.g., competitive binding studies.

Methods for producing specific antibodies against a peptide of interest and for purifying the peptides or antibodies are conventional. The peptides used for generation of the antibodies can be produced by a variety of methods, including isolating them from purified proteins that have been cleaved with a suitable enzymatic or chemical method. Alternatively, the peptides can be produced using conventional chemical synthesis techniques, such as those described, e.g., in G. Barony et al., The Peptides: Analysis, Synthesis & Biology, Academic Press, pp. 3-285 (1980). Some chemically synthesized peptides can be obtained from commercial suppliers. Alternatively, a peptide of the invention can be produced recombinantly, using conventional genetic engineering techniques.

Generally, a peptide against which antibodies are to be produced is isolated or substantially purified before it is used to stimulate antibody formation. The term "substantially purified," as used herein refers to a molecule, such as a peptide, that is substantially free of other proteins, peptides, lipids, carbohydrates, nucleic acids and other biological materials with which it is naturally associated. For example, a substantially pure compound, such as a peptide, can be at least about 60%, by dry weight, preferably at least about 70%, 80%, 90%, 95%, or 99% the molecule of interest. Methods for isolating (purifying) proteins or peptides are conventional.

An "antibody," as used herein, can be, e.g., polyclonal, monoclonal (mAb), recombinant, humanized or partially humanized, chimeric, single chain, Fab, or fragments of such antibodies. Other specific binding partners, such as aptamers, can also be used. The antibody can be of any isotype, e.g., IgM, various IgG isotypes such as $IgG_1$, $IgG_{2a}$, etc., and it can be from any animal species that produces antibodies, including goat, rabbit, mouse, chicken or the like. A mixture of antibody types can be used. It is noted that antibodies raised against purified peptides, even polyclonal antibodies, will exhibit high degrees of specificity for a cognate peptide.

Antibodies can be prepared according to conventional methods, which are well known in the art. See, e.g. Green et al., Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988). Methods of preparing humanized or partially humanized antibodies, antibody fragments, etc. and methods of purifying antibodies, are conventional.

Another aspect of the invention is a composition comprising two (or more) unique peptide identifiers for distinguishing two (or more) forms of a protein of interest. In one embodiment, the composition comprises unique peptide identifiers for distinguishing more than one protein and its variants. Such a composition can be used, e.g., to generate antibodies that are specific for the unique peptide identifiers. The antibodies may be of any of the types discussed herein, or combinations thereof.

Another aspect of the invention is a kit for carrying out any of the methods of the invention. For example, one embodiment is a kit for detecting the presence of unique peptide identifiers of interest in a sample. In one embodiment of the invention, a kit comprises one or more antibodies that are specific for one or more unique peptide identifiers and, optionally, means for storing or packaging the antibodies. The antibodies may be in a lyophilized form or in liquid form; they may be stabilized. Alternatively, a kit may comprises reagents for cleaving proteins in a sample, and/or for analyzing the resulting peptides.

The components of the kit will vary according to which method is being performed. Optionally, the kits comprise instructions (e.g., written instructions) for performing the method. Other optional elements of a kit of the invention include suitable buffers, media components, or the like; containers; or packaging materials. The reagents of the kit may be in containers in which the reagents are stable, e.g., in lyophilized form or stabilized liquids. The reagents may also be in single use form, e.g., in amounts for detecting unique peptide identifiers from a single sample, or for carrying out a single diagnostic test. Other optional elements of a kit include affinity chromatography columns in various sizes and configurations depending on the number of samples to be processed. The kit components are dependent on what type of detection method is used. For example, an ELISA kit might contain a capture antibody bound to a solid phase surface (e.g., plastic plate or bead) with detection antibodies able to distinguish either form of peptide, whereas a mass spectrometry based kit could include materials to render proteins into peptides, affinity purify the peptides and elute into a suitable medium for detection by mass spectrometry. Other components of a kit can easily be determined by one of skill in the art. Such components may include suitable controls or standards, buffers or other reagents appropriate for constituting a reaction medium allowing the formation of a peptide-antibody complex, etc.

Abbreviations used herein include the following:

| | |
|---|---|
| CNBr- | Cyanogen Bromide |
| CV- | coefficient of variance |
| Da- | Daltons |
| ESI- | electrospray ionization |
| ETOH- | ethanol |
| HPLC- | high performance liquid chromatography |
| KDa- | Kilo Daltons |
| LC- | liquid chromatography |
| LLOQ- | lower limits of quantitation |
| MALDI- | matrix assisted laser desorption ionization |
| MRM- | multiple reaction monitoring |
| MS- | Mass Spectrometry |
| MS/MS- | tandem mass spectrometry |
| NADPH- | |
| RA- | rheumatoid arthritis |
| SCX- | strong cation exchange (chromatography) |
| TRX- | Thioredoxin |
| TRX80- | Truncated Thioredoxin |
| TAM- | TRX80 activated monocyte |
| TCA- | trichloro-acetic acid |
| TOF- | time of flight |
| XIC- | extracted ion chromatograph |

In the foregoing and in the following examples, all temperatures are set forth in uncorrected degrees Celsius; and, unless otherwise indicated, all parts and percentages are by weight.

EXAMPLES

Example I

Materials and Methods

Sample Material. Recombinant human TRX and TRX80 (R&D Systems) were resuspended in dH$_2$O and aliquots were immediately digested or stored at −80° C. until used. Human plasma obtained from presumed healthy control donors was aliquoted immediately upon collection and stored at −80° C. Whole plasma was used for digestion, without any prior protein depletion. Undepleted pigtail macaque CSF samples used had been archived at −80° C. in aliquots from previous studies performed in a well-characterized SIV/macaque model (Zink et al. (2002) *Journal of neurovirology* 8 Suppl 2, 42-48; Clements et al. (20008) *Journal of neurovirology* 14, 309-317; Witwer et al. (2009) *PLoS ONE* 4(12), e8129)). For detection of TRX and TRX 80 in CSF, samples were obtained during the late stage of infection from macaques that were SIV-infected, SIV-infected and treated with the tetracycline derivative minocycline beginning at 12 or 21 days after SIV inoculation, or from uninfected control animals (Zink et al. (2005) *Jama* 293, 2003-2011; Follstaedt et al. (2008) *Journal of neurovirology* 14, 376-388)).

CNBr Digestion. CNBr digestion was performed by a protocol adapted from Samyn and colleagues (Samyn et al. (2005) *Nat Methods* 2, 193-200). Samples of either recombinant proteins, plasma, or CSF were first denatured and reduced with 10 mM dithiothreitol (DTT) in 7 M guanine hydrochloride (GuHCl), 0.3 M Tris, pH 9.0 for 45 minutes at 55° C. Iodoacetemide (55 mM in 200 mM NH$_4$HCO$_3$ [pH 7.0]) was added for alkylation, performed with shaking for 45 minutes in the dark at room temperature. Denatured, alkylated plasma or CSF samples were then precipitated with 20% TCA on ice for ~1 hr followed by a 15 min spin at 10,000×g (4° C.) to obtain a protein pellet. Alternately, recombinant protein samples (typically 5 ug) were desalted by applying to a Prosorb membrane (Applied Biosystems) and washing twice with 100 ul of dH$_2$O. CNBr (10 M solution prepared fresh in acetonitrile, ACN; Sigma) was then added with deionized water and TFA (1:1:3 vol) to the protein pellet resulting from TCA precipitation (in the case of plasma and CSF) or to the protein adhered to a Prosorb membrane (for recombinant protein). TCA precipitated pellets were slowly solubilized with multiple additions of TFA and extensive vortexing before adding CNBr and dH$_2$O. Digestion proceeded overnight at 4° C. in the dark with gentle shaking. After digestion of recombinant proteins on the Prosorb membrane, peptides were extracted in 70% ACN with 0.1% TFA from the membranes through two 30 min incubations at 37° C., then the pooled extracts were dried in a vacuum concentrator. Additional volumes of 70% ACN with 0.1% TFA also were added to the plasma and CSF digests to wash the samples, aiding in the removal of volatile TFA and CNBr during subsequent vacuum concentration.

Evaluation of CNBr Digests by SYPRO staining and Western Blotting. Samples were separated by electrophoresis on 16.5% or 10-20% gradient tris-tricine gels (BioRad). For total protein staining, gels were fixed during two 30 min incubations (50% methanol, 7% acetic acid) with gentle agitation. They were then stained with SYPRO Ruby (60 mL; Pierce) overnight with agitation at room temperature. Stained gels were washed twice for 30 min (10% methanol, 7% acetic acid), followed by a brief rehydration in dH$_2$O. Imaging was performed on a Typhoon phosphorimager (excitation 528 nm, emission 610 BP; GE Healthcare). For western blotting, samples were run on 15% tris-HCl gels (BioRad) and transferred to PVDF membrane (Immobilon P$^{SQ}$; Millipore). Membranes were blocked with 5% milk in TBST for ≧2 hrs at RT, followed by incubation in primary anti-TRX antibody in the same solution overnight at 4° C. (1 µg/mL; R&D Systems). After four washes with TBST, blots were then incubated with HRP conjugated secondary antibody (anti-goat-HRP, DAKO, 1:2000) for 1 hr at room temperature, followed by multiple washes with TBST and chemiluminescent detection using Super Signal West Dura substrate (Pierce).

MALDI Sample Preparation. Digested samples were cleaned over C18 columns prior to direct MALDI analysis or reverse phase separation. OMIX tips (Varian Inc.) or high capacity C18 columns (NEST) were used, dependent on the quantity of protein in a given sample. Digested peptides were re-suspended in 0.1% TFA prior to clean up, then applied to the columns/tips following manufacturers' instructions. After washing, peptides were eluted in 90% ACN+0.1% TFA. They were then dried in a vacuum concentrator before being re-suspended in 70% ACN+0.1% TFA for spotting to MALDI plates, or in 2% ACN, 0.1% TFA (solution A) in preparation for nano reverse-phase liquid chromatography.

MALDI-TOF/TOF Analysis. Samples (0.5 uL) were spotted to stainless steel MALDI plates with an equal volume of saturated alpha-cyano-4-hydroxy-cinnamic acid (CHCA; Sigma, recrystallized in house, or Ultrapure Matrix, Protea Biosciences) matrix solution in 50% ACN+0.1% TFA. 4700 Calibrant mixture (AB SCIEX) was used for plate calibration for all runs, with eight external calibrant spots monitored. Spectra of peptides were detected using an AB SCIEX TOF/TOF 4800 or 5800 system in positive ion mode MS with reflectron averaging 2500 shots. MS/MS was performed using a 2 KeV extraction method with CID turned off. Up to 5000 shots per peptide were obtained with auto quality setting set to stop acquisition once a total signal to noise of 70 is achieved.

HPLC Separations. A Tempo nano-LC system (AB SCIEX) was used for nano-reverse phase chromatography coupled with automated spotting of fractions for MALDI-TOF/TOF analysis. The spotting system consisted of an auto sampler, a two channel three pump true nano-flow liquid chromatography system (Eksigent Technologies) and an electrostatic spotting platform (AB SCIEX). Dried, C18 cleaned, digests of whole plasma with TRX and TRX 80 digests spiked in were re-suspended in Solution A (2% ACN, 0.1% TFA) and 3 µL samples (30 µg) auto injected onto a Merck Chromolith RP-18 column Peptides were separated on column using a 60 minute linear gradient from 2% ACN to 98% ACN at a flow rate of 4 µL/minute. Spotting of the eluted fractions mixed with alpha-cyano-4-hydroxy-cinnamic acid (CHCA) matrix (7 mg/mL in 70% ACN) to a MALDI plate was performed every 6000 ms throughout the gradient. SCX fractionation was performed by the Johns Hopkins Mass Spectrometry and Proteomics Facility using a PolyLC Inc. (Columbia, Md.) PolySULFOETHYL A column (10 cm×2.1 mm, 5 um particle size, 300 Angstrom pore size). 100 µg samples were re-suspended in 2 mL of loading buffer and loaded onto the column in two 1 mL injections followed by a 20 minute load equilibration time. Peptides were eluted at 250 µL/min in a 35 min gradient (3%-100% solvent B) using solvent A (10 mM potassium phosphate in 25% acetonitrile, pH 2.8) and solvent B (350 mM KCl in 10 mM potassium phosphate in 25% acetonitrile, pH 2.8). Absorbance was monitored and fractions were collected in one-minute intervals. Cleaning buffer was injected (1 mL) from 62-65 min and the column was then re-equilibrated for 20-30 min before beginning another fractionation. These fractions were subsequently dried down, and then desalted using C18 tips (OMIX) prior to spotting to a MALDI plate.

MRM Analysis. Isotopically labeled peptides incorporating heavy lysine residues were synthesized (*K; $^{13}C_6$ $^{15}N_2$; New England Peptide) for use as quantitative standards for the two peptides of interest in an MRM assay. Each labeled residue added 8 Da to the peptide, for a total increase of 40 Da for the TRX peptide (PTFQFF*K*KGQ*KVGEFSGAN*KE*KLEATINELV (SEQ ID NO:34), 3525 Da), and 8 Da for the TRX80 peptide (PTFQFF*K (SEQ ID NO:35), 922 Da). MRM experiments were performed on a QqLIT triple quadrupole mass spectrometer (QTRAP® 5500 system or 4000 QTRAP®, AB SCIEX). MRMPilot™ software (AB SCIEX) was used to guide the initial development of MRM transitions. All charge states of the precursor ions were first determined, transitions were then chosen for each following optimization with changing collision energy. LC separation methods were developed for LC MRM using high flow conditions on a Shimadzu LC-20AD. Preliminary determination of limits of detection for the two peptides in buffer were performed with separation on a conventional R2/10 (2.1×100 mm) Poros column (Life Technologies), with a 5 min gradient from 5-95% ACN+0.1% formic acid. For detection of the peptides in the matrix of CNBR-digested plasma, various chromatography chemistries and methods were evaluated, and a Unison UK-C8 column (4.6 mm×150 mm) was found to give good resolution, as well as the potential for increased sample capacity. Transitions also were re-evaluated in the matrix of digested plasma and optimized for maximal detection without interference. A summed MRM transition was developed for TRX80, and three other transitions chosen to monitor TRX. Limits of quantitation (LOQ) were then determined for the two peptides of interest in plasma; lower limit of quantitation, LLOQ is defined by % CV<20% and accuracy of 80-120%.

Example II

Results

Diagnostic Peptides to Track and Quantitate TRX and TRX80

Using available protein sequence information for human TRX (NCBI), we determined that chemical cleavage of TRX and TRX80 with CNBr would yield two peptides common to both forms, but also would result in the creation of an additional, unique, identifying peptide for each (FIG. 1). This is not the case for the more regularly employed enzymatic method of tryptic digestion, for which all peptides produced from TRX80 also would be common to TRX. Searches for both of these identifying peptide sequences using BLASTp show that they are non-redundant to other known human protein sequences, making them unique identifiers (Altschul et al. (1997) *Nucleic Acids Res* 25, 3389-3402). Thus, a workflow in which a complex sample that contains TRX and/or TRX80 is reduced, alkylated, and then treated with CNBr can be used to produce a complex peptide mixture. These two unique peptides then can be tracked in this mixture to determine the amounts of TRX and/or TRX80 in the sample.

Figure 6:
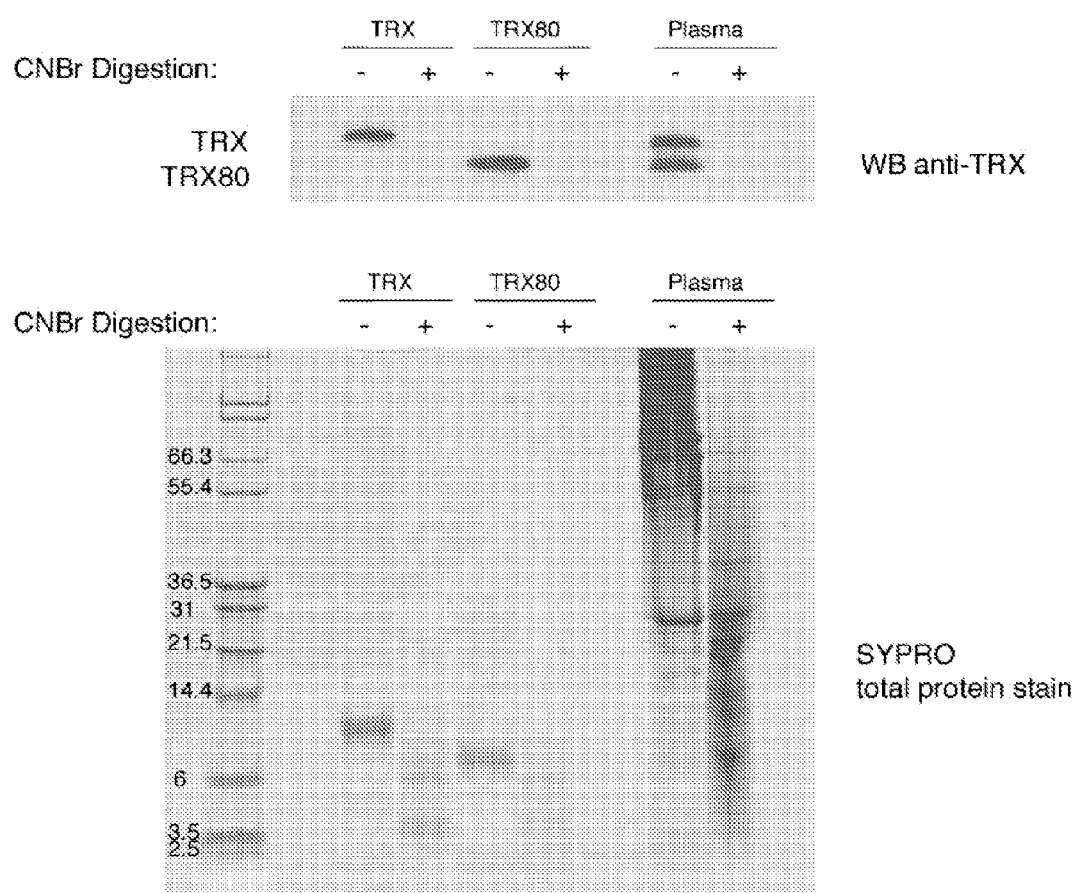
FIG. 6 shows protein digestion with CNBr. Western blot shows the detection of intact TRX and TRX 80 with an anti-thioredoxin antibody (individually, and spiked into plasma), and the loss of immunoreactivity with CNBr digestion, supporting effective cleavage both in buffer and in the matrix of plasma (top). Parallel total protein staining (SYPRO Ruby) shows that recombinant TRX and TRX 80 are effectively digested by CNBr (bottom, representative gel). Expected fragment masses with CNBr digestion are 3484, 3951, and 4390 Da for TRX, and 914, 3951, 4390 Da for TRX 80 (with cysteine alkylation, and homoserine lactone [HSL] formation due to CNBr digestion). A 914 kDa band could not be resolved, although it was later detected by MS. Digestion of the spiked plasma also is illustrated, showing a general loss of high molecular weight protein species and an increase in low molecular weight peptides.

When samples of recombinant TRX or TRX80 were digested with CNBr, the proteins were neither detectable by western blot, nor were bands of the whole proteins (at approximately 12 and 10 kDa, respectively) visible in a total protein stained gel, both indicating that they were effectively digested (FIG. 6). Digestion of human plasma spiked with TRX and TRX80 (10 ng/µL) showed effective cleavage of these proteins in the matrix of plasma, as well as overall cleavage of total protein, illustrated by a loss of very high molecular weight species and an increase in low molecular weight polypeptides.

Figures 7C, 7D:
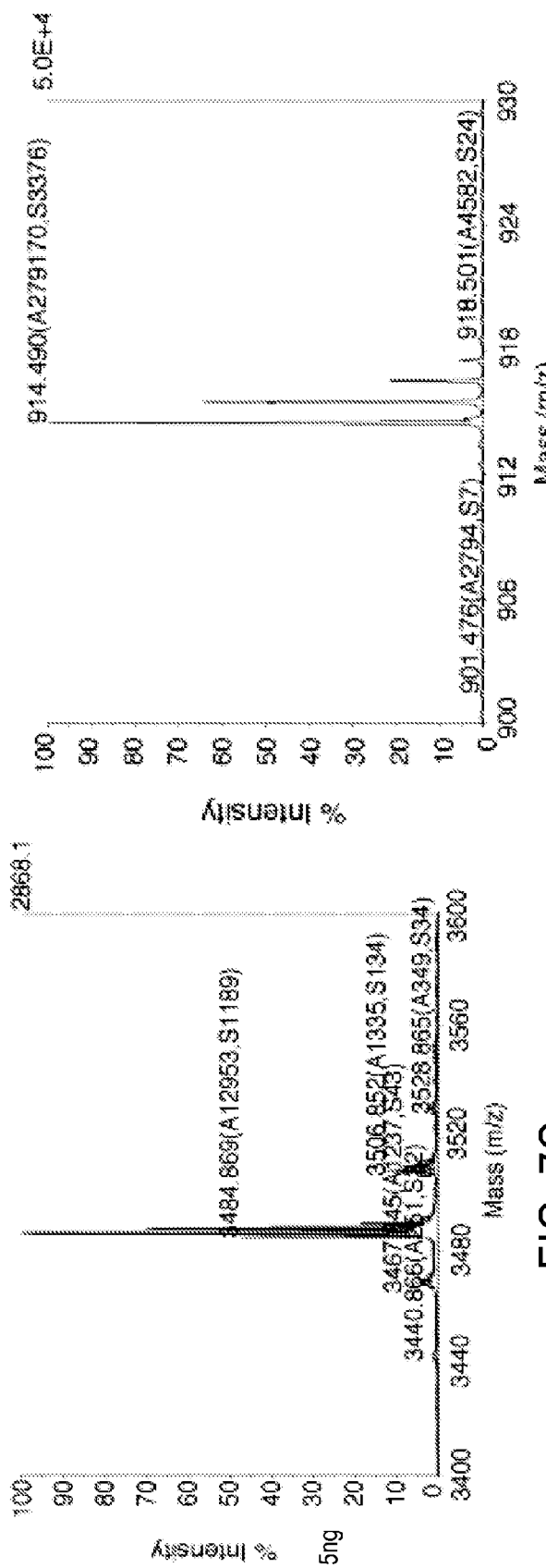
Figures 7E, 7F:
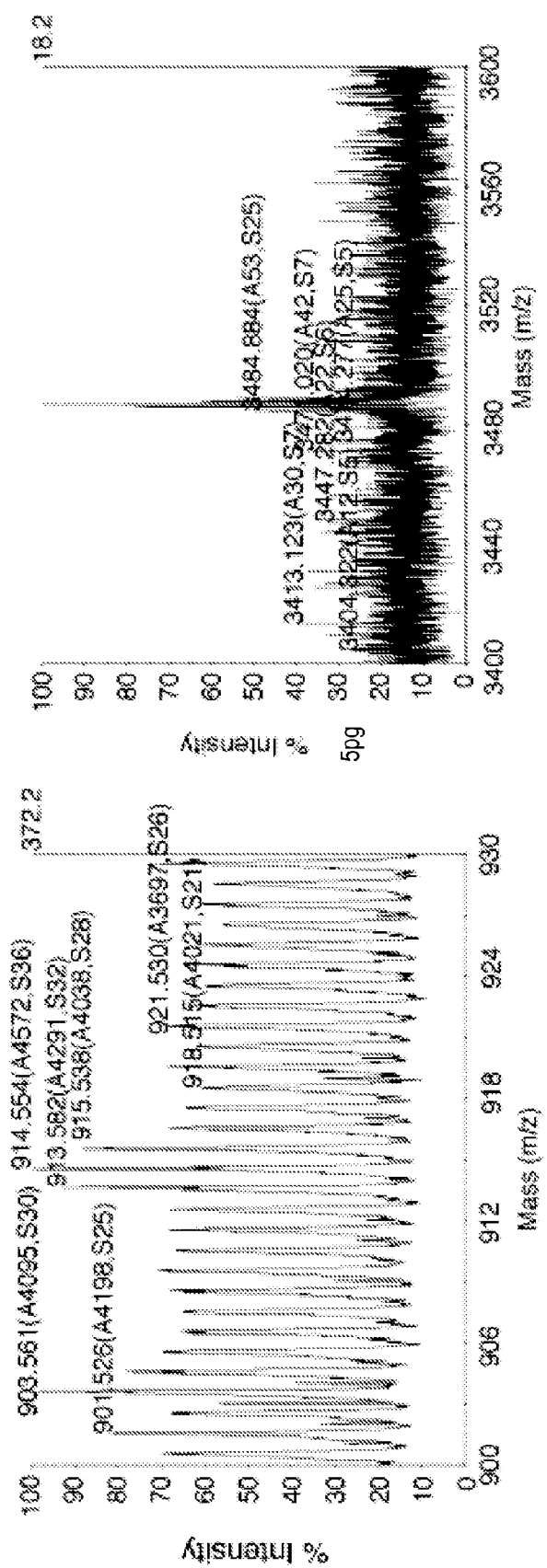

Following CNBr digestion of recombinant TRX and TRX80, peaks corresponding to the expected unique peptide masses were detected for each by MALDI (FIG. 1). Both peptides ionized efficiently, and were detectable from digests of consecutive tenfold dilutions of purified recombinant protein, from 50 ng to 5 pg, spotted directly to a MALDI plate and crystallized with alpha-cyano-4-hydroxy-cinnamic acid (CHCA) matrix (FIG. 7). The identities of these peptides were confirmed by obtaining MS/MS spectra and verified with theoretical masses for product ions.

Figure 8:
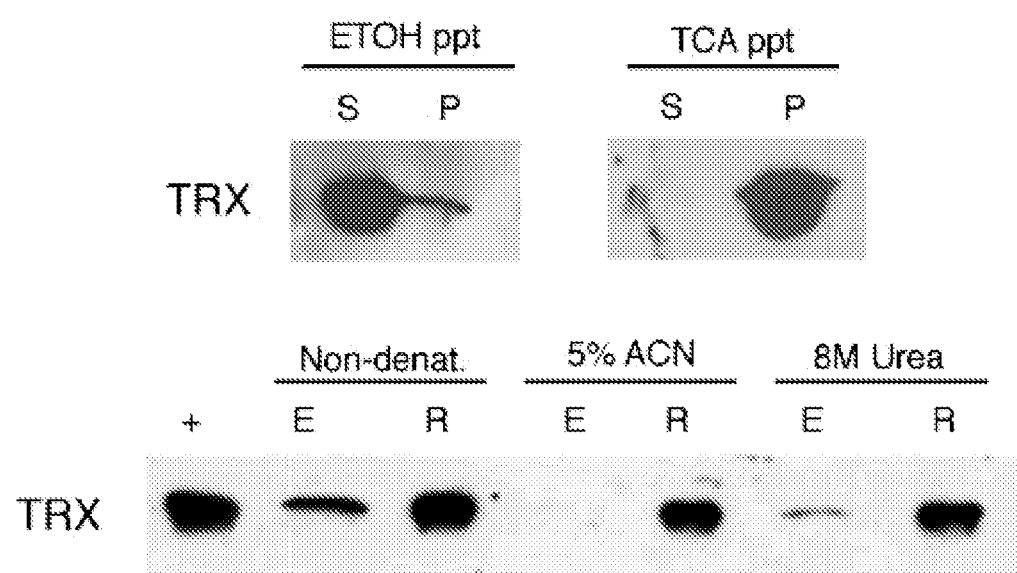
FIG. 8 shows sample fractionation methods. The localization of TRX (spiked into whole plasma at a concentration of 2 ng/µL) was tracked through several different sample preparation procedures by western blotting (representative blots shown). Samples were precipitated by ETOH or by TCA, and equivalent portions of the supernatant (S) and pellet (P) analyzed (top). Samples denatured in several different ways were then also subjected to spin filtration (YM-50 Microcon filter), and equivalent portions of the eluent (E) and retentate (R) were analyzed (bottom). MALDI spectra showing the benefits of immunodepletion of keratin peptides from a sample.
Figure 9A:
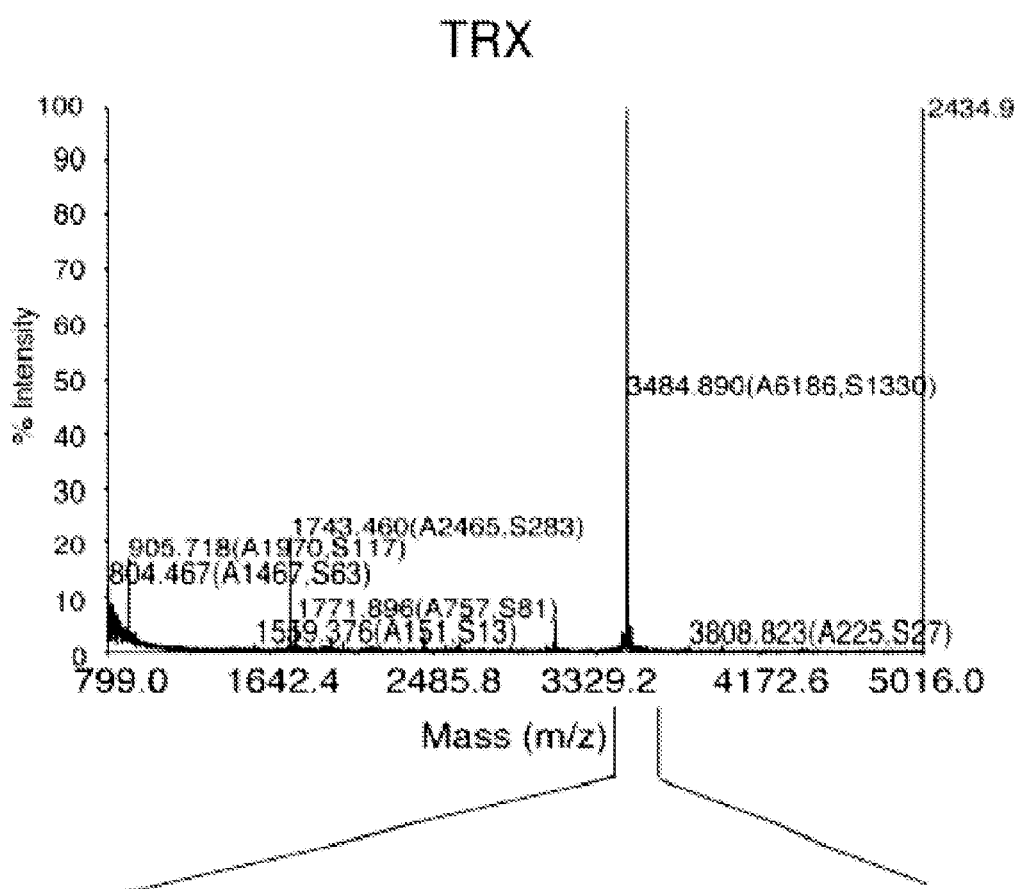
FIGS. 9A-9F shows HPLC-MS detection of digested TRX and TRX 80. Elution times for nano-reverse phase LC were determined for the two peptides of interest. The identifying peptide for TRX 80 (914 KDa) consistently eluted at 25.75 minutes on a 60 minute linear gradient, while that for TRX (3484 KDa) eluted at 35.55 minutes. CNBr digests of recombinant TRX and TRX 80 were spiked into 100 µg of CNBr-digested whole human plasma, in consecutive tenfold dilutions. The mixture was then examined by LC-MS. Both peptides of interest were detected at levels down to 10 ng from within the complex plasma mixture (representative spectra shown, experiment performed in duplicate).
Figure 9B:
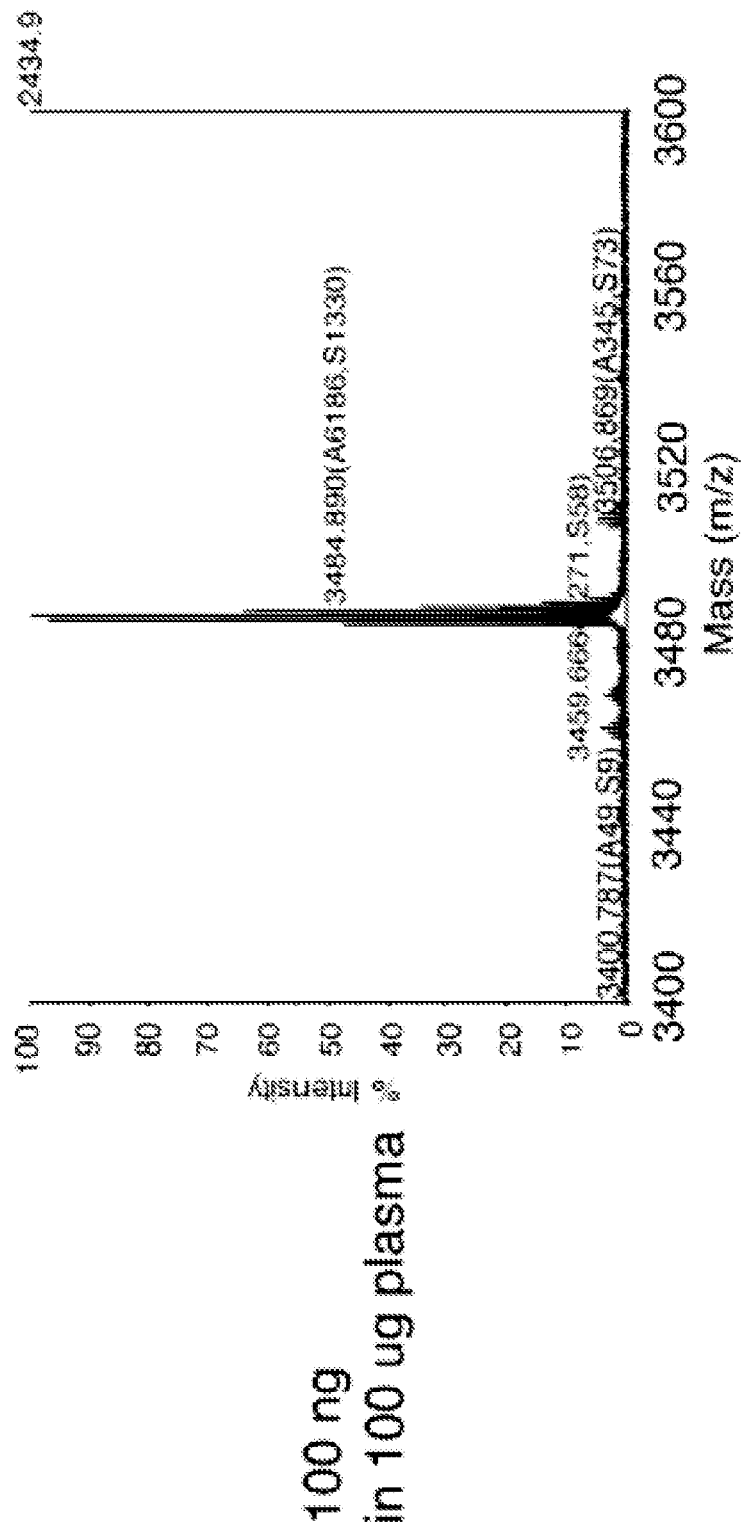
Figure 9C:
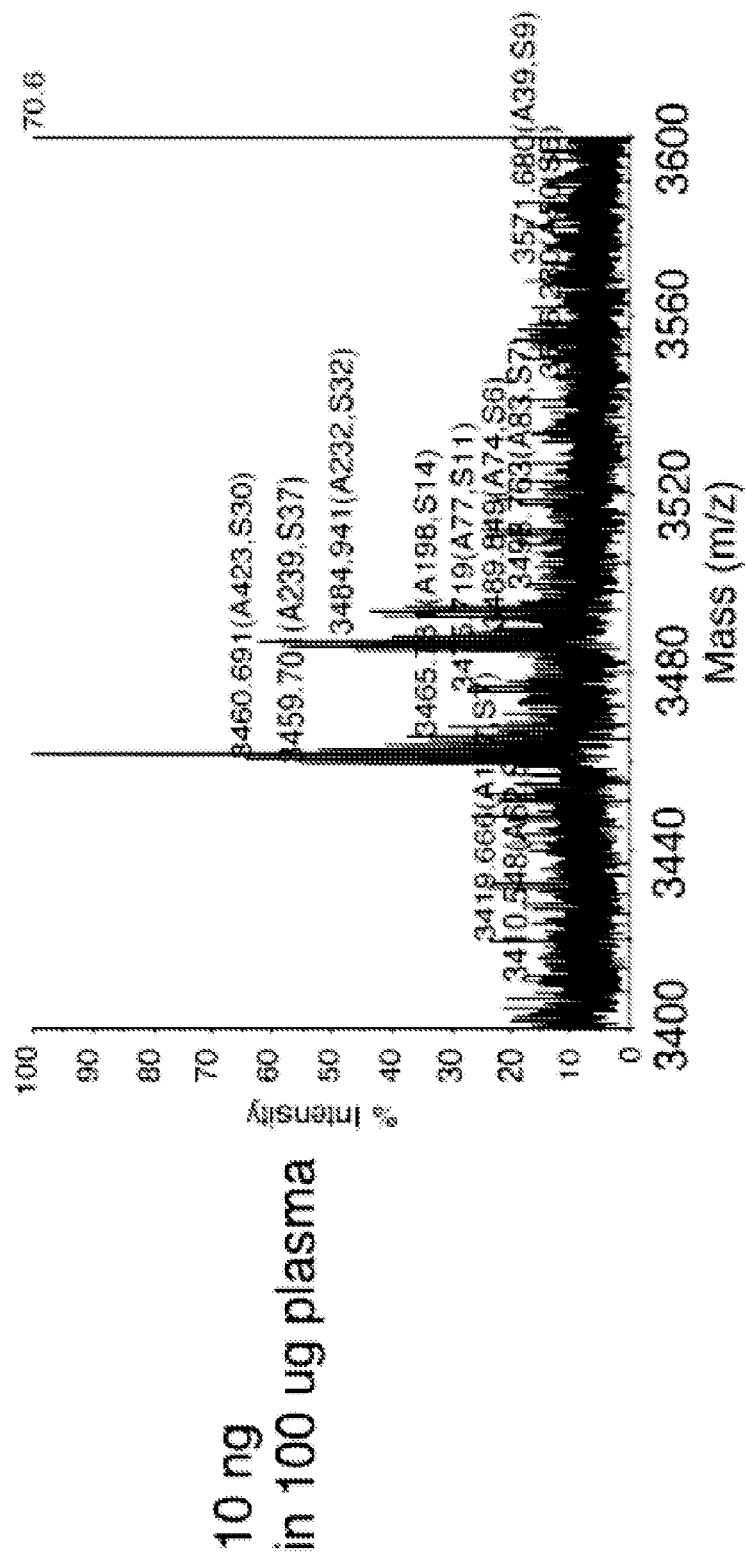
Figure 9D:
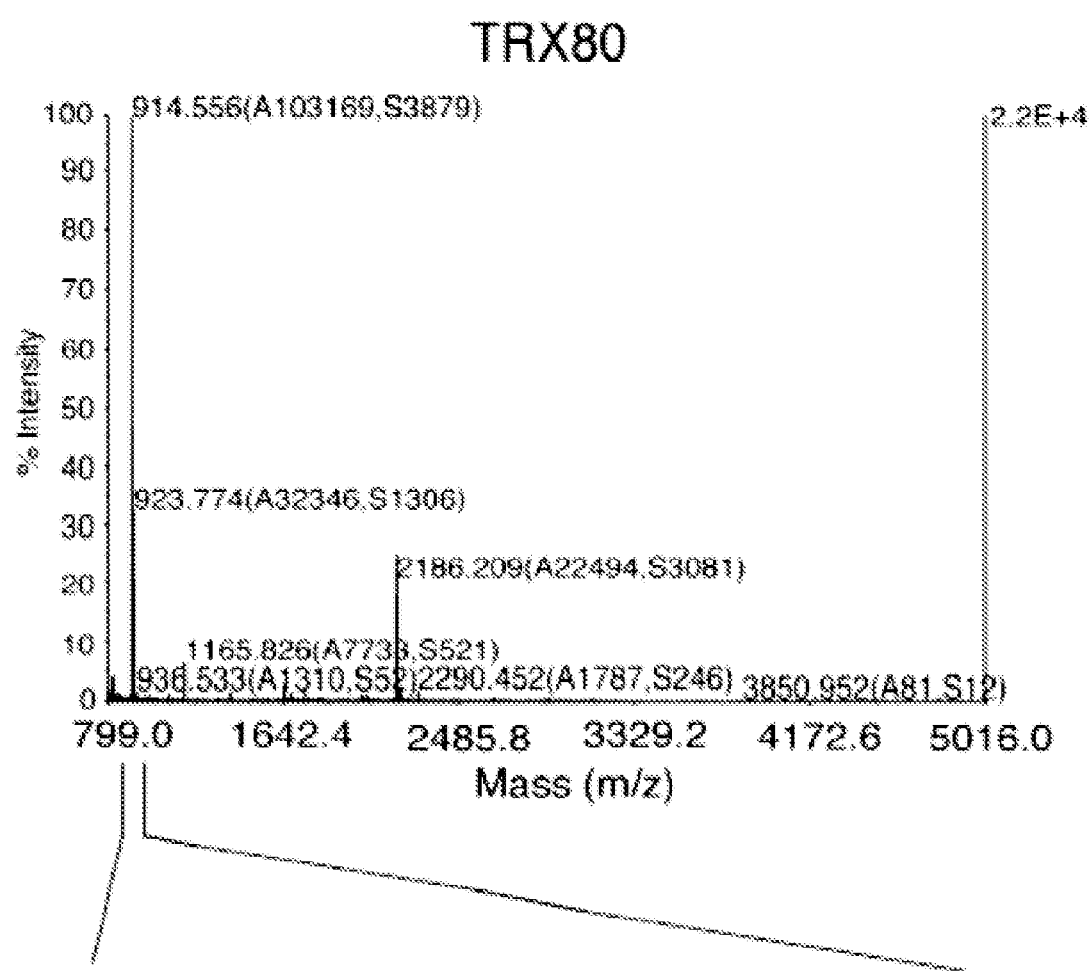
Figure 9E:
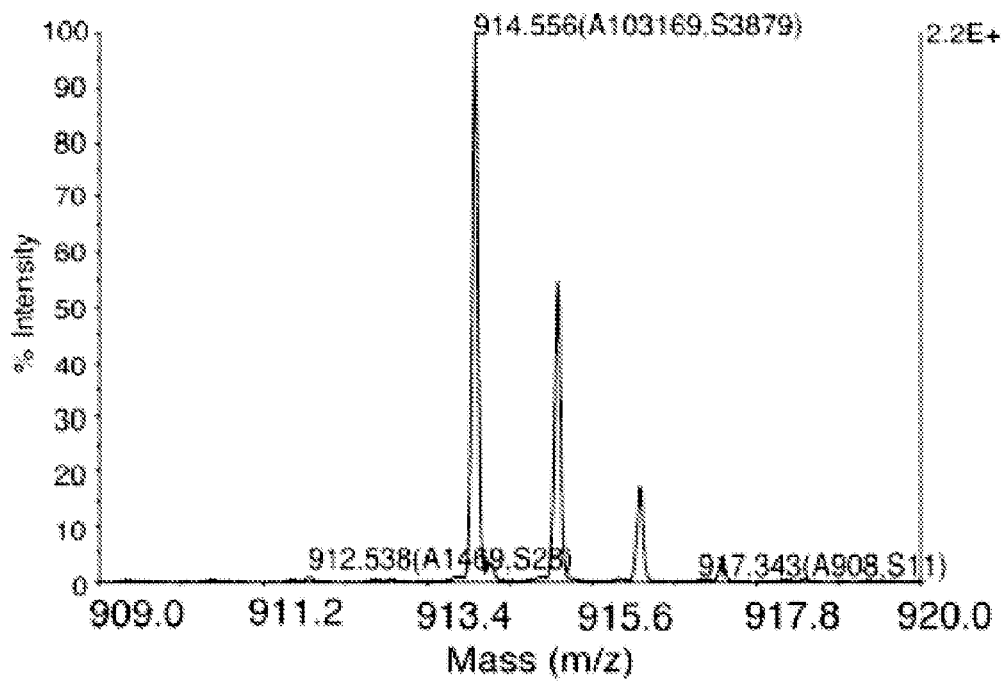
Figure 9F:
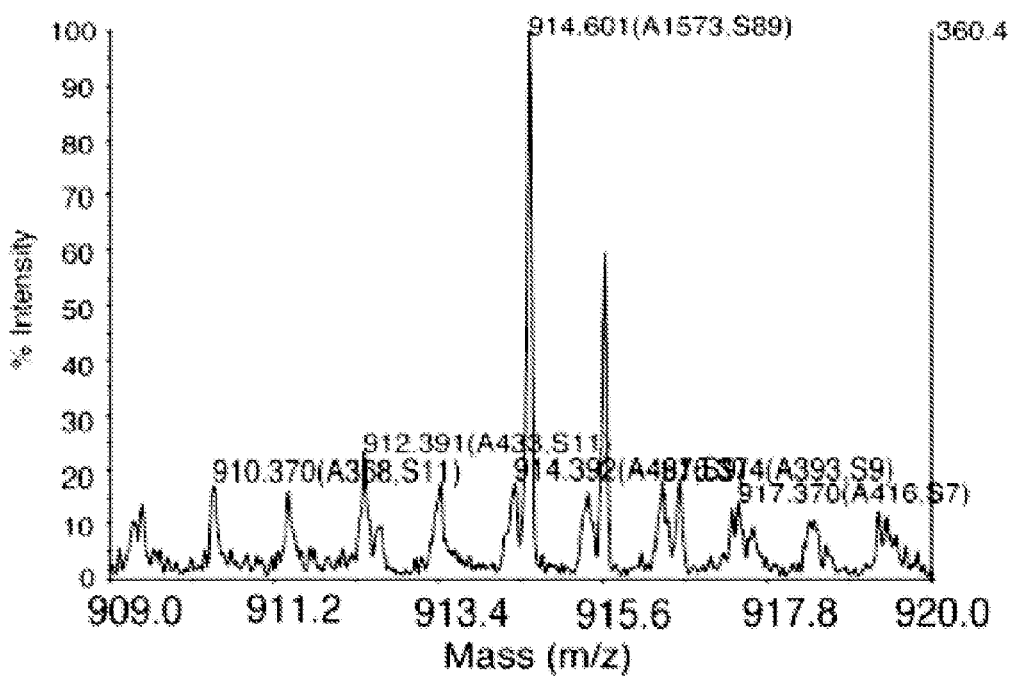
Figure 10A:
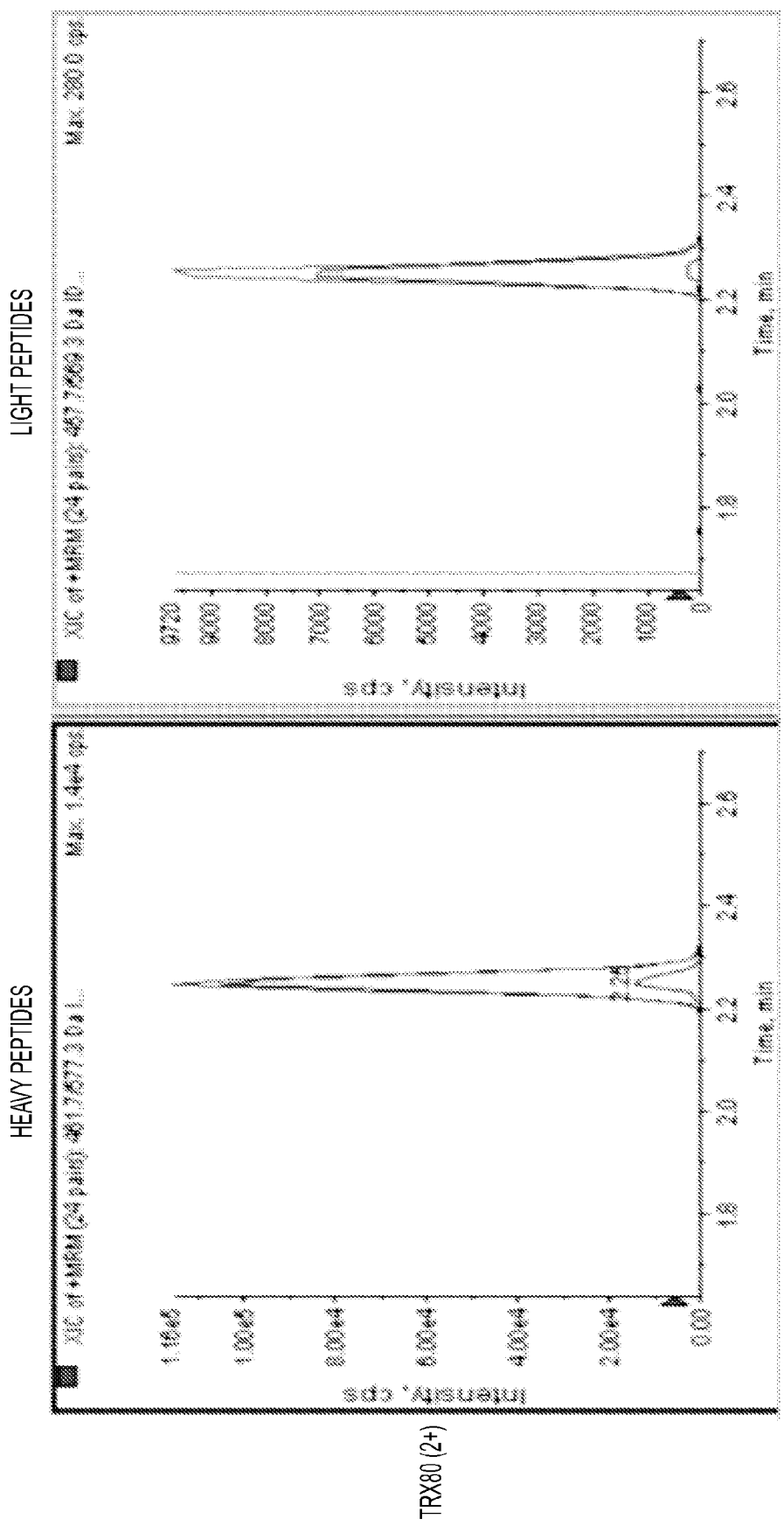
FIGS. 10A-10D shows the detection of TRX and TRX 80 by LC-MRM. All charge states of the two peptides of interest were identified, and MRM transitions were then developed and optimized for each parent ion on the 4000 QTRAP system. XICs obtained from an LC-MRM assay of 50 fmole of both heavy and light peptides are shown. Lower limits of quantitation (LLOQs) of 1-5 fmole and 500 amole were obtained for TRX and TRX 80, respectively in buffer. Conventional high-flow chromatography was used (R2/10 Poros column, AB).
Figure 10B:
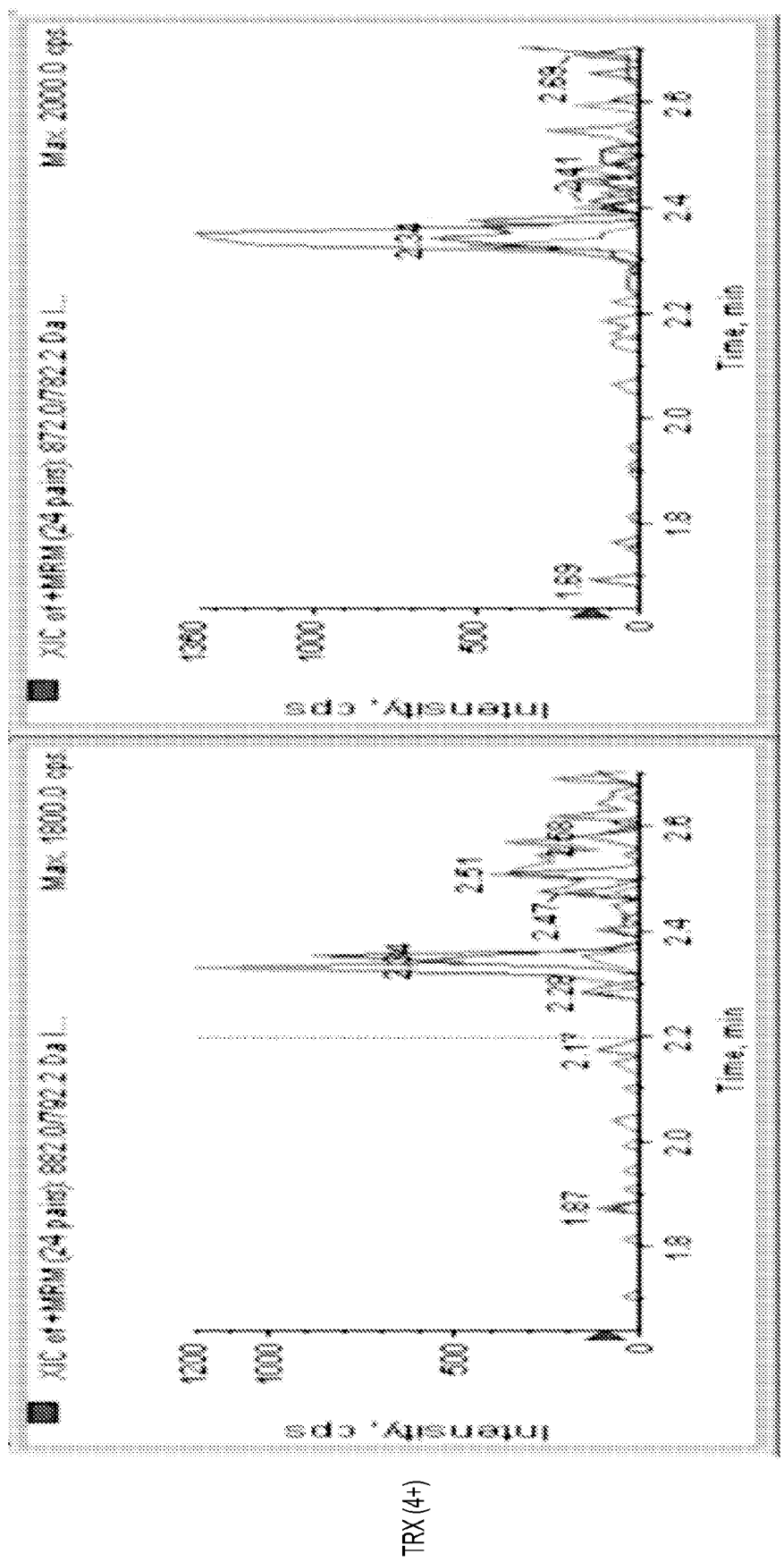
Figure 10C:
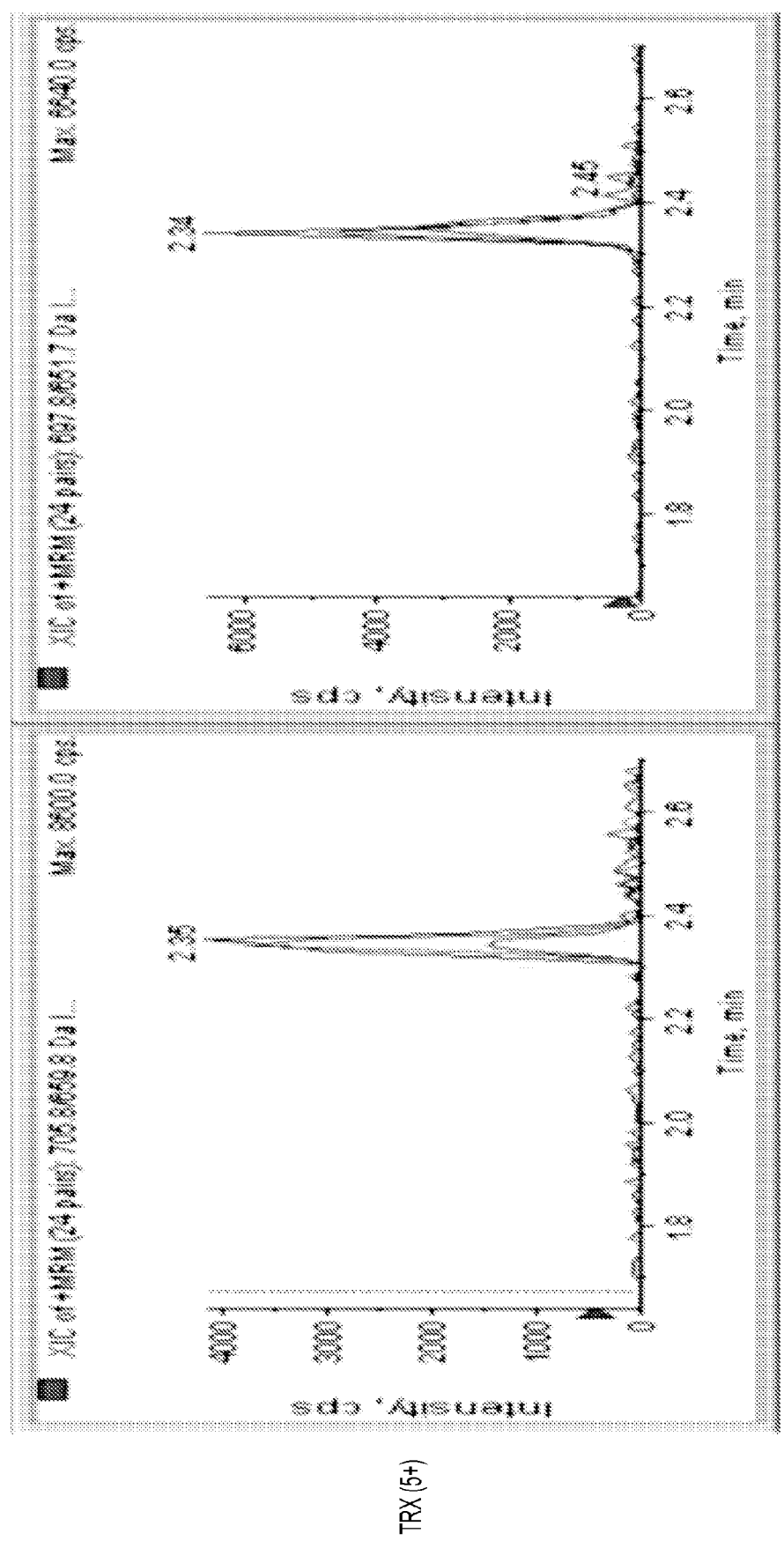
Figure 10D:
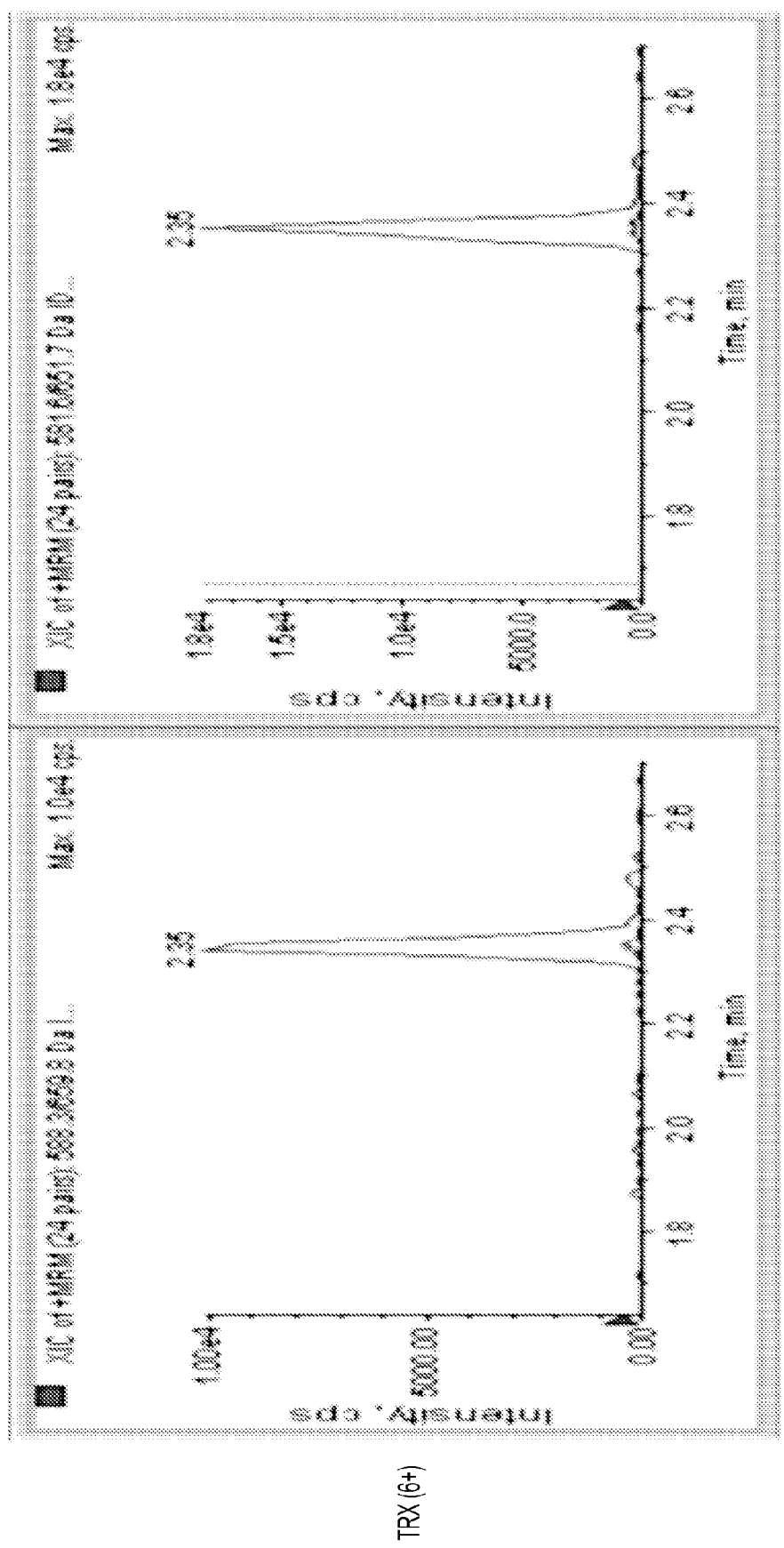

Despite the very low absolute detection level attained by MALDI for these peptides, in the complex mixture of peptides produced from the digestion of whole human plasma, the peptides quickly become obscured, even at much higher levels. Attempts to overcome sample complexity and dynamic range issues, including specific protein depletion or enrichment methods and the use of crude fractionation of a total protein sample by molecular weight cut-off spin columns, were hindered due to strong interactions of TRX with other proteins. The use of ethanol precipitation to deplete an enriched albumin fraction (Colantonio et al. (2005) *Proteomics* 5, 3831-3835; Fu et al. (2005) *Proteomics* 5, 2656-2664) was found to be inappropriate in this study. Even with prior denaturation (with 10 mM DTT in 7 M GuHCl), TRX remained albumin-associated and was found in both fractions (FIG. 8). This suggests that other methods of albumin depletion may also remove TRX from the sample. TCA precipitation, while not useful for fractionating a sample, did successfully bring TRX into a protein pellet. We also attempted several methods of simplifying samples with spin columns Even using a relatively high molecular weight cut-off spin filtration unit far above the size of our proteins of interest (Microcon YM-50; Millipore), we were unable to get the majority of TRX spiked into test plasma samples (at 2 ng/µL) to successfully elute in a low molecular weight plasma protein fraction, even when samples were denatured with GuHCL, Urea, or ACN. A majority of the TRX protein remained in the high molecular weight retentate under the conditions we examined (FIG. 8). Because of this, we determined that denaturing and digestion of the complete complex sample to obtain smaller peptides prior to performing fractionation would be necessary for accurate quantitation.

Sample Fractionation by Nano-reverse Phase LC and Strong Cation Exchange (SCX)

Using nano-reverse phase HPLC for separation after protein digestion, we determined elution times for the two identifying CNBr peptides on a 60 min linear gradient (approximately 25.75 and 36.55 min for TRX80 and TRX, respectively). We then were able to detect these peptides at low levels when CNBr-digested recombinant TRX and TRX80 were spiked into CNBr digests of whole human plasma, down to a limit of detection (LOD) of 10 ng/100 µg plasma protein (FIG. 9). Fractionation increased detection of the desired peptides by MALDI due to ionization suppression by other abundant species. The LOD was, however, still higher than that obtained for MALDI analysis of digests of the recombinant proteins alone, and higher than that which would be predicted as necessary to detect both proteins in plasma samples under most biological conditions.

SCX fractionation separation of samples also was examined. When separated with a 35 min gradient from 0-350 mM KCl, the peptides for TRX80 and TRX consistently eluted in very narrow windows (centered on 9 and 34 minutes into the gradient, respectively). Samples with decreasing levels of digested recombinant TRX and TRX80 spiked into CNBr-digested plasma were fractionated, and for each sample several fractions surrounding these elutions were evaluated by MALDI. By this method, TRX was consistently detected down to a level of 10 ng/100 ug plasma. A slight gain in sensitivity was obtained for TRX80, with MS/MS verified detection at 1 ng/100 ug plasma (FIG. 2). Ultimately, a new MS platform for a more robust, sensitive assay based on the same CNBr digestion concept was necessary. We developed an MRM assay on a hybrid triple quadrupole/linear ion trap instrument.

MRM Assay for TRX and TRX80

To develop an assay for absolute quantitation, labeled standard peptides containing heavy lysine (*K; $^{13}C_6$ $^{15}N_2$) were produced (FIG. 1). The charge states for heavy (quantitative standard) and light (endogenous) versions of both peptides were determined and their fragmentation spectra obtained on a 4000 QTRAP system. Three MRM transitions then were selected from the fragmentation data for each of these parent ions, optimized for maximal intensity under variable collision energies (FIG. 10). The assay development was performed by MRMPilot software, including some transitions for the larger TRX peptide that were manually optimized. An LC method was optimized for the effective retention and separation of these peptides for LC-MRM. High flow chromatography was used in order to develop a more robust method compared to nano-flow; such a method could then more readily be adapted for high throughput analysis of large sample sets in the lab or clinic. Additionally, the greater column capacity makes it possible for more total sample to be run, if necessary, to detect low-level analytes.

Using these methods on the 4000 QTRAP instrument, limits of quantitation for both TRX and TRX80 by LC-MRM in buffer were determined. The TRX80 peptide was detected to a limit of ~500 amoles, while TRX was detected at ~1-5 fmoles on column. This suggested that absolute detection of levels in the targeted range of low nanograms of the proteins is possible. However, detection in the matrix of plasma once again resulted in a higher level of background and potential for suppression.

To obtain a gain in sensitivity during optimization of a method for detection of these two peptides in CNBr-digested plasma, this work was migrated to the QTRAP 5500 system. The transitions developed were examined in the context of plasma, and re-optimized to account for matrix effects. Several different approaches to chromatography also were examined, and a Unison UK-C8 column (4.6 mm×150 mm) was found to provide optimal binding and separation of the CNBr plasma digest. LC-MRM was performed and transitions were monitored for dilutions of heavy standard peptides in CNBr-digested plasma to obtain standard concentration curves (dilutions of 1-10,000 fmole peptide in 2 µL of plasma protein). Two MRM transitions were monitored for the TRX80 peptide, and it was determined that the best sensitivity was obtained by summing the MRM transitions together for quantitation. Three MRM transitions also were used for TRX and these were used separately. When detection curves were produced in triplicate, lower limits of quantitation (LLOQ, defined by CV<20% and accuracy between 80-120%) were identified at 10 and 2 fmole for TRX and TRX80, respectively, in 2 uL CNBr-digested plasma. This is equivalent to detection of the proteins in plasma at levels of 59 ng/mL TRX and 9 ng/mL TRX80. XICs are shown for the LLOQ (FIG. 3).

Assaying TRX and TRX80 in Macaque CSF by MRM

Given that previously reported biological range of TRX in plasma extends slightly below the LLOQ reached in this assay, we decided to evaluate the assay in a matrix with lower interference. We chose to examine CSF, where TRX and TRX80 might provide insight into inflammatory CNS disease processes. As protein concentration and variation is generally far lower in CSF than plasma, we hypothesized that we would readily be able to detect TRX or TRX80 in CSF.

Figure 4A:
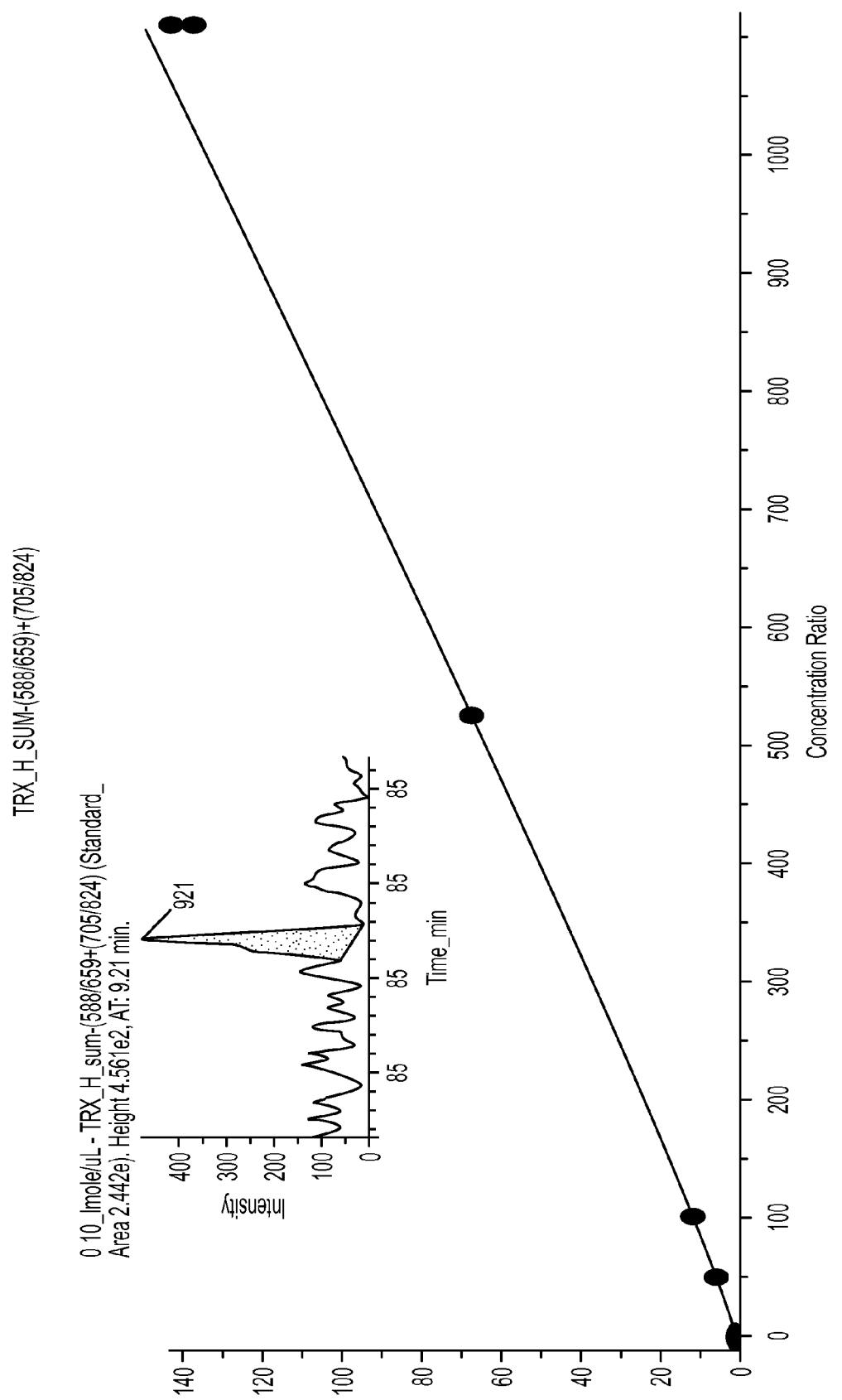
Figure 4B:
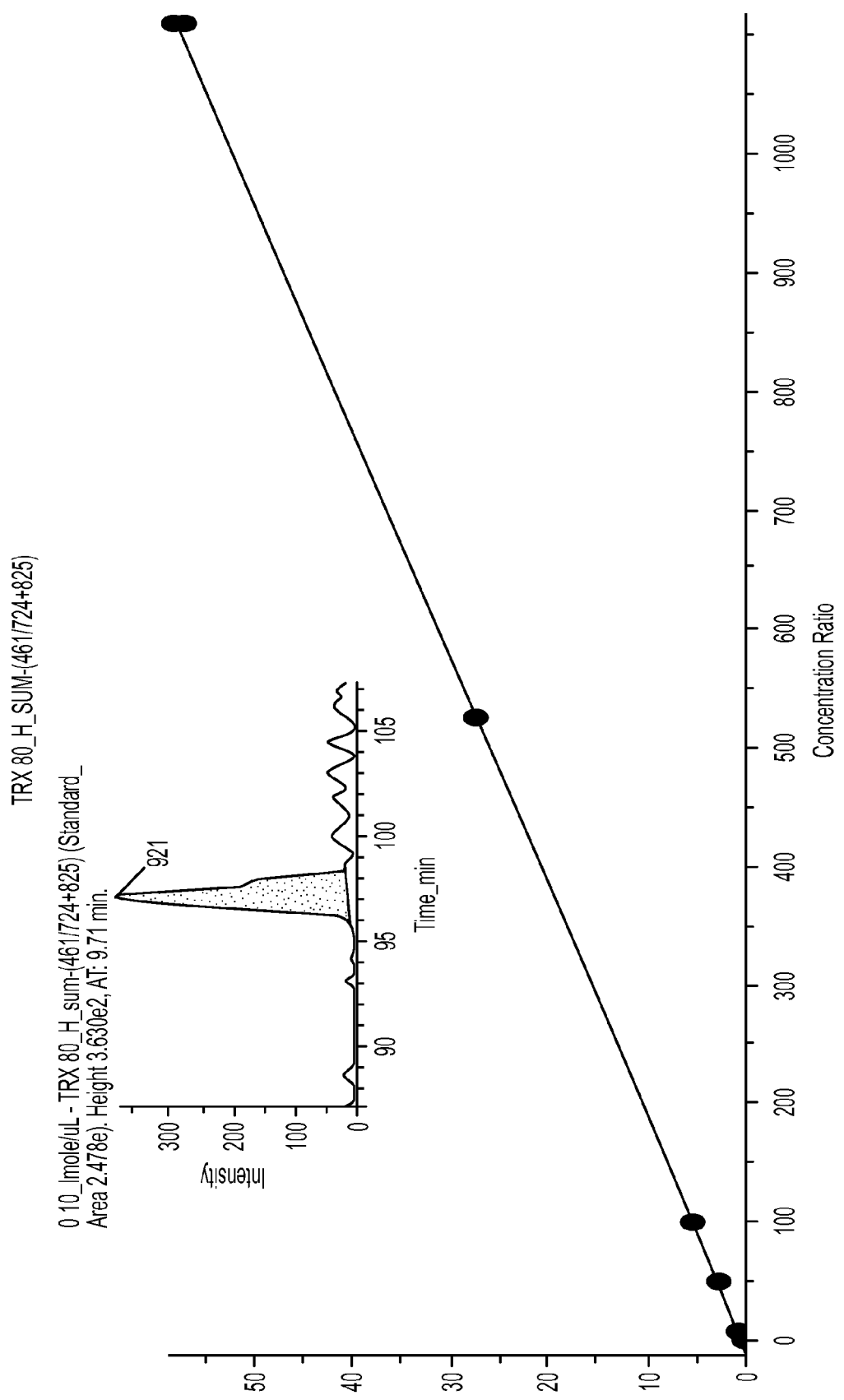

Since TRX levels have been shown to be elevated peripherally in HIV infection (Nakamura et al. (1996) *Int Immunol* 8, 603-611), we asked whether TRX might also be present in the CSF of SIV-infected macaques with encephalitis (Follstaedt et al. (2008) (supra)). The macaque TRX protein sequence is highly conserved with the human protein; the sequences of the two peptides of interest were identical. Detection curves were produced using pooled, CNBr-digested CSF samples as a matrix. LLOQs for the two peptides were identified at 1 fmole/µL for TRX and 0.5 fmole/µL for TRX80 (FIG. 4).

Figure 5:
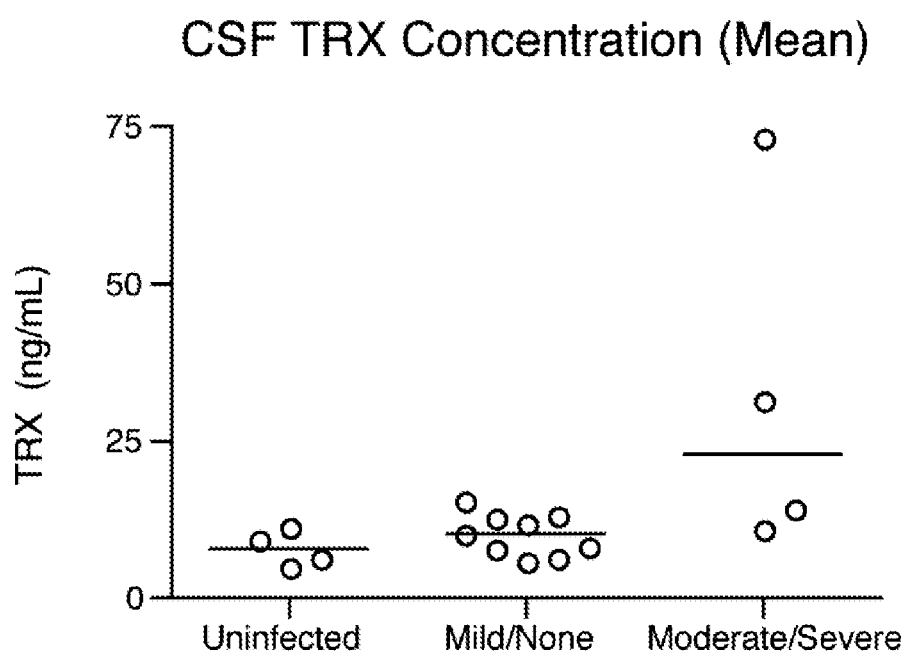
FIG. 5 shows CSF TRX levels measured by MRM. TRX was measured in CSF samples from uninfected, SIV-infected, and SIV-infected minocycline treated macaques that went on to develop either mild/none or moderate/severe encephalitis. Group median values are displayed for each group (bar) Animals that developed moderate or severe encephalitis had significantly elevated levels of CSF TRX (p=0.05; Mann-Whitney).

Seventeen individual macaque CSF samples were evaluated using this MRM assay: four uninfected control animals, eight SIV-infected untreated animals, and five SIV-infected animals treated with the drug minocycline as a potential anti-HIV, neuroprotective therapeutic (Zink et al. (2005) (supra)). Individual CNBr-digested CSF samples were spiked with heavy labeled reference peptides prior to assaying in triplicate. While TRX was identified at varying levels in all samples, the presence of TRX80 was not identified in any sample. It is possible that TRX80 levels in these samples fall <LOD for the assay. While there were no significant differences observed in the levels of TRX between minocycline-treated and untreated animals (not shown), when all animals were grouped by their encephalitis status, a significant difference existed between SIV-infected animals that developed no/mild encephalitis versus animals that developed moderate/severe encephalitis (FIG. 5, P=0.05, Mann-Whitney).

Discussion

In this study we demonstrated that CNBr digestion of samples containing TRX produces identifying peptides that can be used to monitor both TRX and TRX80. Standard protein fractionation methods are not effective for concentrating TRX in a simplified fraction due to the presence of the protein in multiple fractions. Thus, separation at the peptide level is necessary to prevent sample preparation biases. Using a peptide-level separation and identification method provided several advantages, bypassing protein-protein interaction concerns that can interfere in accurate quantitation and protein fractionation problems.

Although TRX and TRX80 were detectable by MALDI, even with RP-LC or SCX separation prior to MS, the sensitivity necessary for plasma assay was not attainable on this platform. Given the complex mixture of peptides produced from the digestion of whole human plasma, the target peptides quickly become suppressed, even when present at much higher abundance. MALDI based methods are expected to provide an effective assay for other samples such as synovial fluid or cerebrospinal fluid, which have decreased complexity. Given our goal of quantitating TRX and TRX80 in plasma, the move to a new MS platform for a more advanced, robust, sensitive assay based on the same CNBr digestion concept was necessary. We began development of an MRM assay on a hybrid triple quadrupole/linear ion trap instrument.

The goal of distinguishing TRX from TRX80 imposed the unique restriction on this MRM assay of pre-defining specific peptides to be examined for each form of the protein, as all transitions for each form had to be obtained from its single respective parent ion. Extensive validation was performed to show a solid MRM assay for quantitation, and multiple transitions were used for each single peptide. A recent study (Fortin et al. (2009) *Mol Cell Proteomics* 8, 1006-15) gave proof-of-principle for quantitation under such conditions, demonstrating the ability to develop an accurate, precise assay based on only one peptide after extensive assay validation to quantitate PSA to low ng/mL levels in serum using high flow LC.

In this study, LODs 100-times lower than those obtained by MALDI were reached by MRM, allowing for quantitation of levels in the ng/mL range (LLOQs 59 ng/mL TRX, 9 ng/mL TRX80). This is within the range observed in human plasma (Pekkari et al. (2000) *J Biol Chem* 275, 37474-37480; Baker et al. (2006) *J Lab Clin Med* 147, 83-90). The QTRAP 5500 system permits sensitive detection in plasma, and provides the option of further developing a multiple reaction monitoring cubed (MRM$^3$) assay (Fortin et al. (2009) *Anal Chem* 81, 9343-9352) for higher specificity. The use of high-flow chromatography conditions in conjunction with the assay also permits increased sample capacity, if necessary. Digestion with CNBr makes this option very cost effective in contrast to the more expensive enzymatic digestion of large volume samples. High-flow chromatography also is a robust method that will allow this LC-MRM assay to be adapted for high-throughput use and multiplex quantitation with other biomarkers.

The biology of the TRX/TRX80 system is of broad interest to many different areas of research. TRX has been shown to play a role in many disease processes, and these continue to be very active areas of study. Elevated levels of secreted TRX in disease may provide some degree of protection from damaging oxidative radicals by way of its antioxidant properties. Administration of exogenous TRX as a potential therapeutic strategy has been evaluated in models of myocardial ischemia-reperfusion injury, cerebral ischemia, interstitial lung disease, chronic obstructive pulmonary disease, and others as a potential therapeutic strategy (Burke-Gaffney et al. (2005) *Trends Pharmacol Sci* 26, 398-404; Kinoshita et al. (2007) *Biochem Biophys Res Commun* 354, 712-719). However, its ability to protect against oxidative stress could be confounded by its potential to contribute to inflammatory immune processes, particularly if conditions favor its cleavage to TRX80. In many of the disease conditions in which there is elevated secreted TRX, it still is unclear whether it is contributing further to the pathology by affecting cell signaling processes, or is a response to oxidative stress of other disease processes, or possibly both. To elucidate TRX's potentially protective and harmful properties, the ability to quantitatively track TRX and TRX80 in biological systems is important.

Little is known of the roles of TRX and TRX80 in HIV infection. Plasma levels of TRX increase with progressing HIV infection, correlating with increased disease severity and lowered CD4+ T cell counts (Nakamura et al. (1996) *Int Immunol* 8, 603-611). TRX80 levels have not been examined in HIV infection, although an in vitro study showed that addition of exogenous TRX80 enhances HIV replication in macrophage cultures (Newman et al. (1994) *J Exp Med* 180, 359-363.) TRX could be an important component in modulating the phenotype and activation of peripheral monocytes and T cells in HIV infection. Activated cells of the monocyte lineage play a key role in the development of HIV-associated organ-specific diseases, such as CNS disease. Here we investigated TRX levels in CSF samples from an SIV/macaque model of HIV-associated neurological disease. TRX was detectable in CSF by this method, and secreted TRX was significantly higher in SIV-infected animals that develop moderate/severe encephalitis than in animals that develop no/mild encephalitis.

We were unable to convincingly identify TRX80 in these samples. There are several potential reasons for this, including the timing at which the samples were obtained during the disease model, the possibility that the cleavage site is not truly at the predicted 80 AA, or that TRX80 may not be present in the CSF under the conditions studied. Evaluation of samples collected longitudinally during disease progression should provide insight into oxidative stress and inflammatory processes, and help evaluate potential therapeutics for HIV CNS disease.

Understanding basic TRX related processes can shed light onto the regulation of oxidative stress both in health and in disease. This continually growing area of research will benefit from tools such as this MRM assay to monitor the proteins involved in an accurate, sensitive way.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, particularly with regard to the specific finding for which they are referenced herein, and in the figures, are hereby incorporated in their entirety by reference.

We claim:

1. A method for detecting a full-length protein and a truncated form thereof, in a sample, comprising the steps of:
    optionally denaturing and/or reducing proteins in the sample;
    cleaving the proteins into smaller peptides; and
    detecting a unique peptide identifier for the full-length protein and/or a unique peptide identifier for the truncated protein, in the sample, wherein the full length protein is thioredoxin (TRX), and the truncated protein is its biologically active, C-terminal truncated, 10 kDa cleavage product, TRX 80, and wherein the unique peptide identifier for TRX is PTFQFFKKGQKVGEFS-GANKEKLEATINELV (SEQ ID NO:1), and the unique peptide identifier for TRX 80 is PTFQFFK (SEQ ID NO:2).

2. The method of claim 1, wherein proteins in the sample are cleaved by a chemical cleavage method or with a protease, and the N-terminal peptides from the full-length and the truncated protein are different, and can serve as unique peptide identifiers for the two proteins.

3. The method of claim 2, wherein the chemical cleavage method is cleavage at aspartyl residues by formic acid, cyanogen bromide cleavage, or 2-iodosobenzoic acid cleavage (IBA).

4. The method of claim 2, wherein the protease is trypsin, chymotrypsin, or Lys-C.

5. The method of claim 1, wherein proteins in the sample are cleaved by a chemical cleavage method or with a protease, and the C-terminal peptides from the full-length and the truncated protein are different, and can serve as unique peptide identifiers for the two proteins.

6. The method of claim 5, wherein the chemical cleavage method is cleavage at aspartyl residues by formic acid, cyanogen bromide cleavage, or 2-iodosobenzoic acid cleavage (IBA).

7. The method of claim 5, wherein the protease is trypsin, chymotrypsin, or Lys-C.

8. The method of claim 1, wherein proteins in the sample are optionally denatured and reduced and are then cleaved by chemical cleavage or with a protease, and the C-terminal peptides from the full-length and the truncated protein are different, and can serve as unique peptide identifiers for the two forms of the protein.

9. The method of claim 8, wherein proteins in the sample are denatured and reduced and are then cleaved with cyanogen bromide, to produce, among other peptides common to the two forms of the protein, the unique peptide identifiers represented by SEQ ID NO:1 and SEQ ID NO:2.

10. The method of claim 1, wherein the unique peptide identifiers are detected by HPLC, ELISA, electrochemiluminescence, flow cytometry, based bead assays, mass spectrometry (MS), a multiple reaction monitoring assay (MRM), or selective reaction monitoring assay (SRM).

11. The method of claim 1, wherein the unique peptide identifiers are detected by mass spectrometry.

12. The method of claim 1, which is quantitative.

13. The method of claim 1, wherein the sample is a cell homogenate, a tissue homogenate, a biopsy tissue homogenate, serum/plasma, cerebrospinal fluid (CSF), synovial fluid, urine, cardiac tissue, tears, saliva, or culture medium in which cells have been grown.

14. A kit for carrying out the method of claim 1.

* * * * *

SEQUENCE LISTING

<160> NUMBER OF SEQ ID NOS: 35

<210> SEQ ID NO 1
<211> LENGTH: 31
<212> TYPE: PRT
<213> ORGANISM: Homo sapiens

<400> SEQUENCE: 1

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile Asn Glu Leu Val

<210> SEQ ID NO 2
<211> LENGTH: 7
<212> TYPE: PRT
<213> ORGANISM: Homo sapiens

<400> SEQUENCE: 2

Pro Thr Phe Gln Phe Phe Lys
1               5

<210> SEQ ID NO 3
<211> LENGTH: 105
<212> TYPE: PRT
<213> ORGANISM: Homo sapiens

<400> SEQUENCE: 3

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 4
<211> LENGTH: 81
<212> TYPE: PRT
<213> ORGANISM: Homo sapiens

<400> SEQUENCE: 4

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys

<210> SEQ ID NO 5
<211> LENGTH: 36
<212> TYPE: PRT
<213> ORGANISM: Homo sapiens

<400> SEQUENCE: 5

Val Lys Gln Ile Glu Ser Lys Thr Ala Phe Gln Glu Ala Leu Asp Ala
1               5                   10                  15

Ala Gly Asp Lys Leu Val Val Asp Phe Ser Ala Thr Trp Cys Gly
            20                  25                  30

```
Pro Cys Lys Met
        35

<210> SEQ ID NO 6
<211> LENGTH: 37
<212> TYPE: PRT
<213> ORGANISM: Homo sapiens

<400> SEQUENCE: 6

Ile Lys Pro Phe Phe His Ser Leu Ser Glu Lys Tyr Ser Asn Val Ile
1               5                   10                  15

Phe Leu Glu Val Asp Val Asp Asp Cys Gln Asp Val Ala Ser Glu Cys
            20                  25                  30

Glu Val Lys Cys Met
        35

<210> SEQ ID NO 7
<211> LENGTH: 31
<212> TYPE: PRT
<213> ORGANISM: Homo sapiens

<400> SEQUENCE: 7

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile Asn Glu Leu Val
            20                  25                  30

<210> SEQ ID NO 8
<211> LENGTH: 30
<212> TYPE: PRT
<213> ORGANISM: Homo sapiens

<400> SEQUENCE: 8

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile Asn Glu Leu
            20                  25                  30

<210> SEQ ID NO 9
<211> LENGTH: 29
<212> TYPE: PRT
<213> ORGANISM: Homo sapiens

<400> SEQUENCE: 9

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile Asn Glu
            20                  25

<210> SEQ ID NO 10
<211> LENGTH: 28
<212> TYPE: PRT
<213> ORGANISM: Homo sapiens

<400> SEQUENCE: 10

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile Asn
            20                  25

<210> SEQ ID NO 11
<211> LENGTH: 27
```

-continued

<212> TYPE: PRT
<213> ORGANISM: Homo sapiens

<400> SEQUENCE: 11

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile
            20                  25

<210> SEQ ID NO 12
<211> LENGTH: 26
<212> TYPE: PRT
<213> ORGANISM: Homo sapiens

<400> SEQUENCE: 12

Pro Thr Phe Gln Phe Phe Lys Lys Gly Gln Lys Val Gly Glu Phe Ser
1               5                   10                  15

Gly Ala Asn Lys Glu Lys Leu Glu Ala Thr
            20                  25

<210> SEQ ID NO 13
<211> LENGTH: 25
<212> TYPE: PRT
<213> ORGANISM: Homo sapiens

<400> SEQUENCE: 13

Pro Thr Phe Gln Phe Phe Lys Lys Gly Gln Lys Val Gly Glu Phe Ser
1               5                   10                  15

Gly Ala Asn Lys Glu Lys Leu Glu Ala
            20                  25

<210> SEQ ID NO 14
<211> LENGTH: 24
<212> TYPE: PRT
<213> ORGANISM: Homo sapiens

<400> SEQUENCE: 14

Pro Thr Phe Gln Phe Phe Lys Lys Gly Gln Lys Val Gly Glu Phe Ser
1               5                   10                  15

Gly Ala Asn Lys Glu Lys Leu Glu
            20

<210> SEQ ID NO 15
<211> LENGTH: 23
<212> TYPE: PRT
<213> ORGANISM: Homo sapiens

<400> SEQUENCE: 15

Pro Thr Phe Gln Phe Phe Lys Lys Gly Gln Lys Val Gly Glu Phe Ser
1               5                   10                  15

Gly Ala Asn Lys Glu Lys Leu
            20

<210> SEQ ID NO 16
<211> LENGTH: 22
<212> TYPE: PRT
<213> ORGANISM: Homo sapiens

<400> SEQUENCE: 16

Pro Thr Phe Gln Phe Phe Lys Lys Gly Gln Lys Val Gly Glu Phe Ser
1               5                   10                  15

Gly Ala Asn Lys Glu Lys
            20

```
<210> SEQ ID NO 17
<211> LENGTH: 21
<212> TYPE: PRT
<213> ORGANISM: Homo sapiens

<400> SEQUENCE: 17

Pro Thr Phe Gln Phe Phe Lys Lys Gly Gln Lys Val Gly Glu Phe Ser
1               5                   10                  15

Gly Ala Asn Lys Glu
            20

<210> SEQ ID NO 18
<211> LENGTH: 20
<212> TYPE: PRT
<213> ORGANISM: Homo sapiens

<400> SEQUENCE: 18

Pro Thr Phe Gln Phe Phe Lys Lys Gly Gln Lys Val Gly Glu Phe Ser
1               5                   10                  15

Gly Ala Asn Lys
            20

<210> SEQ ID NO 19
<211> LENGTH: 19
<212> TYPE: PRT
<213> ORGANISM: Homo sapiens

<400> SEQUENCE: 19

Pro Thr Phe Gln Phe Phe Lys Lys Gly Gln Lys Val Gly Glu Phe Ser
1               5                   10                  15

Gly Ala Asn

<210> SEQ ID NO 20
<211> LENGTH: 18
<212> TYPE: PRT
<213> ORGANISM: Homo sapiens

<400> SEQUENCE: 20

Pro Thr Phe Gln Phe Phe Lys Lys Gly Gln Lys Val Gly Glu Phe Ser
1               5                   10                  15

Gly Ala

<210> SEQ ID NO 21
<211> LENGTH: 17
<212> TYPE: PRT
<213> ORGANISM: Homo sapiens

<400> SEQUENCE: 21

Pro Thr Phe Gln Phe Phe Lys Lys Gly Gln Lys Val Gly Glu Phe Ser
1               5                   10                  15

Gly

<210> SEQ ID NO 22
<211> LENGTH: 16
<212> TYPE: PRT
<213> ORGANISM: Homo sapiens

<400> SEQUENCE: 22

Pro Thr Phe Gln Phe Phe Lys Lys Gly Gln Lys Val Gly Glu Phe Ser
1               5                   10                  15
```

```
<210> SEQ ID NO 23
<211> LENGTH: 15
<212> TYPE: PRT
<213> ORGANISM: Homo sapiens

<400> SEQUENCE: 23

Pro Thr Phe Gln Phe Phe Lys Lys Gly Gln Lys Val Gly Glu Phe
1               5                   10                  15

<210> SEQ ID NO 24
<211> LENGTH: 14
<212> TYPE: PRT
<213> ORGANISM: Homo sapiens

<400> SEQUENCE: 24

Pro Thr Phe Gln Phe Phe Lys Lys Gly Gln Lys Val Gly Glu
1               5                   10

<210> SEQ ID NO 25
<211> LENGTH: 13
<212> TYPE: PRT
<213> ORGANISM: Homo sapiens

<400> SEQUENCE: 25

Pro Thr Phe Gln Phe Phe Lys Lys Gly Gln Lys Val Gly
1               5                   10

<210> SEQ ID NO 26
<211> LENGTH: 12
<212> TYPE: PRT
<213> ORGANISM: Homo sapiens

<400> SEQUENCE: 26

Pro Thr Phe Gln Phe Phe Lys Lys Gly Gln Lys Val
1               5                   10

<210> SEQ ID NO 27
<211> LENGTH: 11
<212> TYPE: PRT
<213> ORGANISM: Homo sapiens

<400> SEQUENCE: 27

Pro Thr Phe Gln Phe Phe Lys Lys Gly Gln Lys
1               5                   10

<210> SEQ ID NO 28
<211> LENGTH: 10
<212> TYPE: PRT
<213> ORGANISM: Homo sapiens

<400> SEQUENCE: 28

Pro Thr Phe Gln Phe Phe Lys Lys Gly Gln
1               5                   10

<210> SEQ ID NO 29
<211> LENGTH: 9
<212> TYPE: PRT
<213> ORGANISM: Homo sapiens

<400> SEQUENCE: 29

Pro Thr Phe Gln Phe Phe Lys Lys Gly
1               5

<210> SEQ ID NO 30
<211> LENGTH: 8
<212> TYPE: PRT
```

-continued

```
<213> ORGANISM: Homo sapiens

<400> SEQUENCE: 30

Pro Thr Phe Gln Phe Phe Lys Lys
1               5

<210> SEQ ID NO 31
<211> LENGTH: 5
<212> TYPE: PRT
<213> ORGANISM: Homo sapiens

<400> SEQUENCE: 31

Pro Thr Phe Gln Phe
1               5

<210> SEQ ID NO 32
<211> LENGTH: 4
<212> TYPE: PRT
<213> ORGANISM: Homo sapiens

<400> SEQUENCE: 32

Pro Thr Phe Gln
1

<210> SEQ ID NO 33
<211> LENGTH: 5
<212> TYPE: PRT
<213> ORGANISM: Streptomyces griseus

<400> SEQUENCE: 33

Phe Tyr Trp Met Leu
1               5

<210> SEQ ID NO 34
<211> LENGTH: 31
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Heavy lysine
<220> FEATURE:
<221> NAME/KEY: MOD_RES
<222> LOCATION: (11)..(11)
<223> OTHER INFORMATION: Heavy lysine
<220> FEATURE:
<221> NAME/KEY: MOD_RES
<222> LOCATION: (20)..(20)
<223> OTHER INFORMATION: Heavy lysine
<220> FEATURE:
<221> NAME/KEY: MOD_RES
<222> LOCATION: (22)..(22)
<223> OTHER INFORMATION: Heavy lysine

<400> SEQUENCE: 34

Pro Thr Phe Gln Phe Phe Lys Lys Gly Gln Lys Val Gly Glu Phe Ser
1               5                   10                  15

Gly Ala Asn Lys Glu Lys Leu Glu Ala Thr Ile Asn Glu Leu Val
                20                  25                  30

<210> SEQ ID NO 35
<211> LENGTH: 7
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Heavy lysine
```

```
<400> SEQUENCE: 35

Pro Thr Phe Gln Phe Phe Lys
1               5
```